United States Patent
Davis et al.

(10) Patent No.: US 12,011,555 B2
(45) Date of Patent: Jun. 18, 2024

(54) GUIDEWIRE WITH CORE CENTERING MECHANISM

(71) Applicant: Scientia Vascular, Inc., West Valley City, UT (US)

(72) Inventors: Clark C. Davis, Holladay, UT (US); Edward J. Snyder, Park City, UT (US); Todd H. Turnlund, Park City, UT (US)

(73) Assignee: Scientia Vascular, Inc., West Valley City, UT (US)

( * ) Notice: Subject to any disclaimer, the term of this patent is extended or adjusted under 35 U.S.C. 154(b) by 558 days.

(21) Appl. No.: 16/742,211

(22) Filed: Jan. 14, 2020

(65) Prior Publication Data

US 2020/0222672 A1 Jul. 16, 2020

Related U.S. Application Data

(60) Provisional application No. 62/792,775, filed on Jan. 15, 2019.

(51) Int. Cl.
*A61M 25/09* (2006.01)

(52) U.S. Cl.
CPC ... *A61M 25/09* (2013.01); *A61M 2025/09091* (2013.01); *A61M 2025/09166* (2013.01); *A61M 2025/09175* (2013.01)

(58) Field of Classification Search
CPC ............ A61M 25/09; A61M 25/09041; A61M 2025/0293; A61M 2025/09091; A61M 2025/09166; A61M 2025/09175; A61M 2025/09075; A61M 2025/09083; A61M 2025/09041; A61M 2025/09116; A61M 2025/09125
See application file for complete search history.

(56) References Cited

U.S. PATENT DOCUMENTS

| | | |
|---|---|---|
| 2,022,065 A | 11/1935 | Wappler |
| 2,187,299 A | 1/1940 | Burkhardt |

(Continued)

FOREIGN PATENT DOCUMENTS

| | | |
|---|---|---|
| AU | 723040 | 12/1997 |
| AU | 733966 | 5/2001 |

(Continued)

OTHER PUBLICATIONS

U.S. Appl. No. 16/212,425, filed Dec. 6, 2018, Christian.

(Continued)

*Primary Examiner* — Alex M Valvis
*Assistant Examiner* — Nidhi N Patel
(74) *Attorney, Agent, or Firm* — WORKMAN NYDEGGER (57) ABSTRACT

The present disclosure relates to guidewire devices with an outer tube and a core. The distal section of the core extends into and is surrounded by the outer tube. One or more centering mechanisms are also disposed within the outer tube and are arranged to fill a portion of the annular space between the core and the inner surface of the tube. The one or more centering mechanisms thereby assist in keeping the distal section of the core axially aligned within the tube, which enables effective control of the device and minimizes undesirable whip movements of the guidewire.

18 Claims, 6 Drawing Sheets

(56) References Cited

U.S. PATENT DOCUMENTS

| | | |
|---|---|---|
| 3,183,702 A | 5/1965 | Zittel |
| 3,572,334 A | 3/1971 | Petterson |
| 3,612,058 A | 10/1971 | Ackerman |
| 3,709,271 A | 1/1973 | Flory |
| 3,782,233 A | 1/1974 | Helm |
| 3,920,058 A | 11/1975 | Walker |
| 4,163,406 A | 8/1979 | Crawford |
| 4,239,069 A | 12/1980 | Zimmerman |
| 4,416,312 A | 11/1983 | Ostberg |
| 4,688,540 A | 8/1987 | Ono |
| 4,719,924 A | 1/1988 | Crittenden |
| 4,801,297 A | 1/1989 | Mueller |
| 4,846,186 A | 7/1989 | Box |
| 4,895,168 A | 1/1990 | Machek |
| 4,989,608 A | 2/1991 | Ratner |
| 5,047,045 A | 9/1991 | Arney et al. |
| 5,069,217 A | 12/1991 | Fleischhacker |
| 5,084,022 A | 1/1992 | Claude |
| 5,095,915 A | 3/1992 | Angelson |
| 5,102,390 A | 4/1992 | Crittenden et al. |
| 5,144,959 A | 9/1992 | Gambale et al. |
| 5,147,317 A | 9/1992 | Shank |
| 5,154,725 A | 10/1992 | Leopold |
| 5,174,302 A | 12/1992 | Palmer |
| 5,315,996 A | 5/1994 | Lundquist |
| 5,326,374 A | 7/1994 | Ilbawi et al. |
| 5,345,945 A | 9/1994 | Hodgson et al. |
| 5,366,464 A | 11/1994 | Belknap |
| 5,372,587 A | 12/1994 | Hammerslag |
| 5,382,259 A | 1/1995 | Phelps |
| 5,385,152 A | 1/1995 | Abele |
| 5,437,288 A | 8/1995 | Schwartz |
| 5,441,483 A | 8/1995 | Avitall |
| 5,506,682 A | 4/1996 | Pryor |
| 5,507,751 A | 4/1996 | Goode et al. |
| 5,551,444 A | 9/1996 | Finlayson |
| 5,554,114 A | 9/1996 | Wallace et al. |
| 5,569,218 A | 10/1996 | Berg |
| 5,573,520 A | 11/1996 | Schwartz |
| 5,573,867 A | 11/1996 | Zafred et al. |
| 5,659,205 A | 8/1997 | Weisser |
| 5,673,707 A | 10/1997 | Chandrasekaran |
| 5,676,659 A | 10/1997 | McGurk |
| 5,685,568 A | 11/1997 | Pirrello |
| 5,685,868 A | 11/1997 | Lundquist |
| 5,690,120 A | 11/1997 | Jacobsen |
| 5,706,826 A | 1/1998 | Schwager |
| 5,741,429 A | 4/1998 | Donadio |
| 5,746,701 A | 5/1998 | Noone |
| 5,792,154 A | 8/1998 | Doan |
| 5,800,454 A | 9/1998 | Jacobsen |
| 5,833,631 A | 11/1998 | Nguyen |
| 5,833,632 A | 11/1998 | Jacobsen |
| 5,842,461 A | 12/1998 | Azuma |
| 5,860,963 A | 1/1999 | Azam |
| 5,876,356 A | 3/1999 | Viera et al. |
| 5,911,715 A | 6/1999 | Berg |
| 5,911,717 A | 6/1999 | Jacobsen |
| 5,916,194 A | 6/1999 | Jacobsen |
| 5,931,830 A | 8/1999 | Jacobsen |
| 5,954,672 A | 9/1999 | Schwager |
| 6,004,279 A | 12/1999 | Crowley |
| 6,014,919 A | 1/2000 | Jacobsen |
| 6,017,319 A | 1/2000 | Jacobsen |
| 6,022,343 A | 2/2000 | Johnson et al. |
| 6,022,369 A | 2/2000 | Jacobsen |
| 6,027,526 A | 2/2000 | Limon et al. |
| 6,027,863 A | 2/2000 | Donadis |
| 6,033,288 A | 3/2000 | Weisshaus |
| 6,033,394 A | 3/2000 | Vidlund |
| 6,056,702 A | 5/2000 | Lorenzo |
| 6,063,101 A | 5/2000 | Jacobsen |
| 6,110,164 A | 8/2000 | Vidlund |
| 6,132,389 A | 10/2000 | Cornish |
| 6,139,511 A | 10/2000 | Huter |
| 6,168,570 B1 | 1/2001 | Ferrera |
| 6,179,828 B1 | 1/2001 | Mottola |
| 6,183,410 B1 | 2/2001 | Jacobsen |
| 6,183,420 B1 | 2/2001 | Douk et al. |
| 6,214,042 B1 | 4/2001 | Jacobsen |
| 6,228,073 B1 | 5/2001 | Noone |
| 6,245,030 B1 | 6/2001 | Dubois |
| 6,251,086 B1 | 6/2001 | Cornelius |
| 6,260,458 B1 | 7/2001 | Jacobsen |
| 6,261,246 B1 | 7/2001 | Pantages et al. |
| 6,273,881 B1 | 8/2001 | Kiemeneij |
| 6,302,870 B1 | 10/2001 | Jacobsen |
| 6,306,105 B1 | 10/2001 | Rooney |
| 6,346,091 B1 | 2/2002 | Jacobsen |
| 6,356,791 B1 | 3/2002 | Westlund |
| 6,402,706 B2 | 6/2002 | Richardson et al. |
| 6,428,489 B1 | 8/2002 | Jacobsen |
| 6,431,039 B1 | 8/2002 | Jacobsen |
| 6,436,056 B1 | 8/2002 | Wang et al. |
| 6,440,088 B1 | 8/2002 | Jacobsen |
| 6,458,867 B1 | 10/2002 | Wang et al. |
| 6,464,651 B1 | 10/2002 | Hiejima et al. |
| 6,492,615 B1 | 12/2002 | Flanagan |
| 6,494,894 B2 | 12/2002 | Mirarchi |
| 6,527,732 B1 | 3/2003 | Strauss |
| 6,527,746 B1 | 3/2003 | Oslund |
| 6,553,880 B2 | 4/2003 | Jacobsen |
| 6,554,820 B1 | 4/2003 | Wendlandt |
| 6,558,355 B1 | 5/2003 | Metzger |
| 6,579,246 B2 | 6/2003 | Jacobsen |
| 6,602,207 B1 | 8/2003 | Mam |
| 6,606,985 B2 | 8/2003 | Negishi |
| 6,610,046 B1 | 8/2003 | Usami et al. |
| 6,627,724 B2 | 9/2003 | Meijs et al. |
| 6,652,508 B2 | 11/2003 | Griffin |
| 6,671,560 B2 | 12/2003 | Westlund |
| 6,766,720 B1 | 7/2004 | Jacobsen |
| 6,805,676 B2 | 10/2004 | Klint |
| 6,866,642 B2 | 3/2005 | Kellerman et al. |
| RE39,018 E | 3/2006 | Azuma |
| 7,024,885 B2 | 4/2006 | Villalobos |
| 7,097,624 B2 | 8/2006 | Campion |
| 7,110,910 B1 | 9/2006 | Deffenbaugh |
| 7,128,718 B2 | 10/2006 | Hojeibane et al. |
| 7,182,735 B2 | 2/2007 | Shireman |
| 7,276,062 B2 | 10/2007 | McDaniel et al. |
| 7,338,345 B2 | 3/2008 | Fujinami |
| 7,421,929 B2 | 9/2008 | French |
| 7,494,474 B2 | 2/2009 | Richardson et al. |
| 7,507,246 B2 | 3/2009 | McGuckin et al. |
| 7,621,880 B2 | 11/2009 | Ryan |
| 7,637,875 B2 | 12/2009 | Itou |
| 7,641,622 B2 | 1/2010 | Satou |
| 7,670,302 B2 | 3/2010 | Griffin |
| 7,699,792 B2 | 4/2010 | Hofmann |
| 7,722,545 B2 | 5/2010 | Bertsch |
| 7,722,552 B2 | 5/2010 | Aimi |
| 7,744,545 B2 | 6/2010 | Aimi |
| 7,747,314 B2 | 6/2010 | Parins |
| 7,753,859 B2 | 7/2010 | Kinoshita |
| 7,766,896 B2 | 8/2010 | Volk |
| 7,769,839 B2 | 8/2010 | Boivie et al. |
| 7,785,273 B2 | 8/2010 | Eskuri |
| 7,789,839 B2 | 9/2010 | Lupton |
| 7,806,837 B2 | 10/2010 | Rasmussen |
| 7,878,984 B2 | 2/2011 | Davis |
| 7,883,474 B1 | 2/2011 | Mirigian |
| 7,914,467 B2 | 3/2011 | Layman et al. |
| 7,942,832 B2 | 5/2011 | Kanuka |
| 7,967,762 B2 | 6/2011 | Corl et al. |
| 7,989,042 B2 | 8/2011 | Obara et al. |
| 8,043,314 B2 | 10/2011 | Noriega et al. |
| 8,048,004 B2 | 11/2011 | Davis et al. |
| 8,105,246 B2 | 1/2012 | Voeller |
| 8,128,579 B2 | 3/2012 | Chen |
| 8,128,580 B2 | 3/2012 | Fujimagari |
| 8,137,293 B2 | 3/2012 | Zhou |
| 8,167,821 B2 | 5/2012 | Sharrow et al. |
| 8,257,279 B2 | 9/2012 | Jacobsen |

(56) References Cited

U.S. PATENT DOCUMENTS

| | | |
|---|---|---|
| 8,292,828 B2 | 10/2012 | Uihlein |
| 8,357,140 B2 | 1/2013 | Majercak |
| 8,376,961 B2 | 2/2013 | Layman |
| 8,377,056 B2 | 2/2013 | Oyola et al. |
| 8,409,114 B2 | 4/2013 | Parins |
| 8,409,169 B1 | 4/2013 | Moss |
| 8,444,577 B2 | 5/2013 | Bunch |
| 8,454,535 B2 | 6/2013 | Majercak |
| 8,460,213 B2 | 6/2013 | Northrop |
| 8,468,919 B2 | 6/2013 | Christian |
| 8,500,658 B2 | 8/2013 | Boyle |
| 8,517,959 B2 | 8/2013 | Kurosawa |
| 8,535,243 B2 | 9/2013 | Shireman |
| 8,540,648 B2 | 9/2013 | Uihlein |
| 8,551,020 B2 | 10/2013 | Chen et al. |
| 8,551,021 B2 | 10/2013 | Voeller |
| 8,622,931 B2 | 1/2014 | Teague |
| 8,622,933 B2 | 1/2014 | Maki |
| 8,636,270 B2 | 1/2014 | Ostrovsky |
| 8,728,075 B2 | 5/2014 | Wu et al. |
| 8,758,269 B2 | 6/2014 | Miyata et al. |
| 8,795,202 B2 | 8/2014 | Northrop |
| 8,795,254 B2 | 8/2014 | Layman |
| 8,821,477 B2 | 9/2014 | Northrop |
| 8,870,790 B2 | 10/2014 | Jacobsen |
| 8,900,163 B2 | 12/2014 | Jacobsen |
| 8,915,865 B2 | 12/2014 | Jacobsen et al. |
| 8,932,235 B2 | 1/2015 | Jacobsen |
| 8,936,558 B2 | 1/2015 | Jacobsen |
| 8,939,916 B2 | 1/2015 | Jacobsen |
| 8,956,310 B2 | 2/2015 | Miyata |
| 9,067,332 B2 | 6/2015 | Lippert |
| 9,067,333 B2 | 6/2015 | Lippert |
| 9,072,873 B2 | 7/2015 | Lippert |
| 9,072,874 B2 | 7/2015 | Northrop |
| 9,254,143 B2 | 2/2016 | Huynh et al. |
| 9,364,589 B2 | 6/2016 | Cage |
| 9,550,013 B2 | 1/2017 | Kawasaki |
| 9,616,195 B2 | 4/2017 | Lippert |
| 9,623,212 B2 | 4/2017 | Tano |
| 9,662,798 B2 | 5/2017 | Christian |
| 9,700,702 B2 | 7/2017 | Tano |
| 9,848,882 B2 | 12/2017 | Lippert |
| 9,950,137 B2 | 4/2018 | Lippert |
| 10,016,210 B2 | 7/2018 | Lenker et al. |
| 10,252,024 B2 | 4/2019 | Northrop |
| 10,363,389 B2 | 7/2019 | Lippert |
| 10,441,746 B2 | 10/2019 | Besselink |
| 10,639,456 B2 | 5/2020 | Peralta |
| 10,675,057 B2 | 6/2020 | Krieger et al. |
| 10,821,268 B2 | 11/2020 | Snyder et al. |
| 10,835,183 B2 | 11/2020 | Sham et al. |
| 11,305,095 B2 | 4/2022 | Snyder et al. |
| 11,317,938 B2 | 5/2022 | Lenker et al. |
| 11,369,351 B2 | 6/2022 | Davis et al. |
| 2001/0009980 A1 | 7/2001 | Richardson et al. |
| 2002/0013540 A1 | 1/2002 | Jacobsen et al. |
| 2002/0019599 A1 | 2/2002 | Rooney |
| 2002/0049392 A1 | 4/2002 | DeMello |
| 2002/0062524 A1 | 5/2002 | Vogland et al. |
| 2002/0068912 A1 | 6/2002 | Merdan |
| 2002/0078808 A1 | 6/2002 | Jacobsen et al. |
| 2002/0082524 A1 | 6/2002 | Anderson |
| 2003/0009208 A1 | 1/2003 | Snyder et al. |
| 2003/0023190 A1 | 1/2003 | Cox |
| 2003/0060732 A1 | 3/2003 | Jacobsen et al. |
| 2003/0069521 A1 | 4/2003 | Reynolds et al. |
| 2003/0069522 A1 | 4/2003 | Jacobsen |
| 2003/0093059 A1 | 5/2003 | Griffin et al. |
| 2003/0125641 A1 | 7/2003 | Jafari et al. |
| 2004/0039371 A1 | 2/2004 | Tockman et al. |
| 2004/0054349 A1 | 3/2004 | Brightbill |
| 2004/0087933 A1 | 5/2004 | Lee |
| 2004/0093060 A1 | 5/2004 | Seguin et al. |
| 2004/0102719 A1 | 5/2004 | Keith et al. |
| 2004/0102720 A1 | 5/2004 | Kellerman et al. |
| 2004/0111044 A1 | 6/2004 | Davis et al. |
| 2004/0122340 A1 | 6/2004 | Vrba et al. |
| 2004/0167437 A1 | 8/2004 | Sharrow et al. |
| 2004/0167440 A1 | 8/2004 | Sharrow et al. |
| 2004/0171996 A1 | 9/2004 | Kiemeneij |
| 2004/0181174 A2 | 9/2004 | Davis |
| 2004/0186485 A1 | 9/2004 | Kear |
| 2004/0193140 A1 | 9/2004 | Griffin |
| 2004/0225292 A1 | 11/2004 | Sasso et al. |
| 2004/0254450 A1 | 12/2004 | Griffin et al. |
| 2005/0054953 A1 | 3/2005 | Ryan |
| 2005/0065456 A1 | 3/2005 | Eskuri |
| 2005/0124976 A1 | 6/2005 | Devens, Jr. et al. |
| 2005/0216049 A1 | 9/2005 | Jones et al. |
| 2005/0274384 A1 | 12/2005 | Tran et al. |
| 2006/0006649 A1 | 1/2006 | Galdonik et al. |
| 2006/0041186 A1 | 2/2006 | Vancalllie |
| 2006/0074442 A1 | 4/2006 | Noriega |
| 2006/0089618 A1 | 4/2006 | McFerran |
| 2006/0112802 A1 | 6/2006 | Fujinami |
| 2006/0121218 A1 | 6/2006 | Obara et al. |
| 2006/0189896 A1 | 8/2006 | Davis et al. |
| 2006/0241519 A1 | 10/2006 | Hojeibane et al. |
| 2006/0262474 A1 | 11/2006 | Chen et al. |
| 2007/0010786 A1 | 1/2007 | Casey et al. |
| 2007/0055302 A1* | 3/2007 | Henry .............. A61B 17/12022 606/200 |
| 2007/0100285 A1 | 5/2007 | Griffin |
| 2007/0112331 A1 | 5/2007 | Weber et al. |
| 2007/0135763 A1 | 6/2007 | Musbach |
| 2007/0142893 A1 | 6/2007 | Buiser et al. |
| 2007/0167876 A1 | 7/2007 | Euteneuer et al. |
| 2007/0185415 A1 | 8/2007 | Ressemann et al. |
| 2007/0208405 A1 | 9/2007 | Goodin et al. |
| 2007/0221230 A1 | 9/2007 | Thompson |
| 2007/0250036 A1 | 10/2007 | Volk |
| 2007/0282270 A1 | 12/2007 | Mathews et al. |
| 2007/0287955 A1 | 12/2007 | Layman et al. |
| 2008/0021347 A1 | 1/2008 | Jacobsen et al. |
| 2008/0021401 A1 | 1/2008 | Jacobsen et al. |
| 2008/0021404 A1 | 1/2008 | Jacobsen et al. |
| 2008/0021406 A1 | 1/2008 | Jacobsen et al. |
| 2008/0033421 A1 | 2/2008 | Davis et al. |
| 2008/0064989 A1 | 3/2008 | Chen et al. |
| 2008/0077049 A1 | 3/2008 | Hirshman |
| 2008/0086854 A1 | 4/2008 | Boyd |
| 2008/0097246 A1 | 4/2008 | Stafford |
| 2008/0097247 A1 | 4/2008 | Eskuri |
| 2008/0097248 A1 | 4/2008 | Munoz |
| 2008/0119869 A1 | 5/2008 | Teague et al. |
| 2008/0122226 A1 | 5/2008 | Madison |
| 2008/0125674 A1 | 5/2008 | Bilecen et al. |
| 2008/0140101 A1 | 6/2008 | Carley et al. |
| 2008/0147170 A1 | 6/2008 | Vrba |
| 2008/0188298 A1 | 8/2008 | Seelig et al. |
| 2008/0188928 A1 | 8/2008 | Salahieh |
| 2008/0200839 A1 | 8/2008 | Bunch et al. |
| 2008/0262474 A1 | 10/2008 | Northrop |
| 2008/0269641 A1 | 10/2008 | O'Shaughnessy et al. |
| 2008/0319525 A1 | 12/2008 | Tieu |
| 2009/0036832 A1 | 2/2009 | Skujins et al. |
| 2009/0036833 A1 | 2/2009 | Parins |
| 2009/0043283 A1 | 2/2009 | Turnlund et al. |
| 2009/0043372 A1 | 2/2009 | Northrop et al. |
| 2009/0043483 A1 | 2/2009 | Abe et al. |
| 2009/0118675 A1 | 5/2009 | Czyscon et al. |
| 2009/0118704 A1 | 5/2009 | Sharrow et al. |
| 2009/0163945 A1 | 6/2009 | Richard et al. |
| 2009/0177119 A1 | 7/2009 | Heidner |
| 2009/0177185 A1 | 7/2009 | Northrop |
| 2009/0254000 A1 | 10/2009 | Layman et al. |
| 2009/0292225 A1 | 11/2009 | Chen et al. |
| 2009/0318892 A1 | 12/2009 | Aboytes et al. |
| 2010/0063479 A1 | 3/2010 | Merddan |
| 2010/0069882 A1 | 3/2010 | Jennings et al. |
| 2010/0114017 A1 | 5/2010 | Lenker et al. |
| 2010/0114302 A1 | 5/2010 | Tzafriri et al. |
| 2010/0139465 A1 | 6/2010 | Christian et al. |

(56) References Cited

U.S. PATENT DOCUMENTS

| | | |
|---|---|---|
| 2010/0145308 A1 | 6/2010 | Layman et al. |
| 2010/0228150 A1 | 9/2010 | Zimmerman |
| 2010/0256527 A1 | 10/2010 | Lippert et al. |
| 2010/0256528 A1 | 10/2010 | Lippert |
| 2010/0256601 A1 | 10/2010 | Lippert et al. |
| 2010/0256602 A1 | 10/2010 | Lippert et al. |
| 2010/0256603 A1 | 10/2010 | Lippert |
| 2010/0256604 A1 | 10/2010 | Lippert |
| 2010/0256605 A1 | 10/2010 | Lippert et al. |
| 2010/0256606 A1 | 10/2010 | Lippert et al. |
| 2010/0318066 A1 | 12/2010 | Miyata et al. |
| 2011/0011226 A1 | 1/2011 | Tsurusawa |
| 2011/0022003 A1 | 1/2011 | Tekulve |
| 2011/0160680 A1 | 6/2011 | Cage et al. |
| 2011/0245807 A1 | 10/2011 | Sakata et al. |
| 2011/0245808 A1 | 10/2011 | Voeller et al. |
| 2011/0251519 A1 | 10/2011 | Romoscanu |
| 2011/0313417 A1 | 12/2011 | De et al. |
| 2012/0065623 A1 | 3/2012 | Nelson, III |
| 2012/0158034 A1 | 6/2012 | Wilson |
| 2012/0209073 A1 | 8/2012 | McWeeney et al. |
| 2012/0239074 A1 | 9/2012 | Aboytes et al. |
| 2012/0271397 A1 | 10/2012 | Muzslay et al. |
| 2012/0289938 A1 | 11/2012 | Northrop et al. |
| 2013/0018359 A1 | 1/2013 | Coyle |
| 2013/0096553 A1 | 4/2013 | Hill et al. |
| 2013/0110000 A1 | 5/2013 | Tully |
| 2013/0131642 A1 | 5/2013 | Miyata et al. |
| 2013/0144267 A1 | 6/2013 | Chan et al. |
| 2013/0184703 A1 | 7/2013 | Shireman et al. |
| 2013/0226033 A1 | 8/2013 | Eskuri |
| 2013/0255456 A1 | 10/2013 | Christian |
| 2013/0274784 A1 | 10/2013 | Lenker et al. |
| 2014/0012281 A1 | 1/2014 | Wang et al. |
| 2014/0031719 A1 | 1/2014 | Kanazawa |
| 2014/0058324 A1 | 2/2014 | Salahieh et al. |
| 2014/0094787 A1 | 4/2014 | Reynolds |
| 2014/0187983 A1 | 7/2014 | Anderson |
| 2014/0257363 A1 | 9/2014 | Lippert |
| 2014/0276109 A1 | 9/2014 | Gregorich |
| 2014/0276117 A1 | 9/2014 | Burkett |
| 2014/0276787 A1 | 9/2014 | Wang et al. |
| 2014/0279109 A1 | 9/2014 | Vasquez et al. |
| 2014/0309657 A1 | 10/2014 | Ben-Ami |
| 2014/0336620 A1 | 11/2014 | Layman et al. |
| 2014/0343538 A1 | 11/2014 | Lenker et al. |
| 2015/0011834 A1 | 1/2015 | Ayala et al. |
| 2015/0011964 A1 | 1/2015 | Abner |
| 2015/0057639 A1 | 2/2015 | Storbeck et al. |
| 2015/0190614 A1 | 7/2015 | Uihlein |
| 2015/0190615 A1 | 7/2015 | Shaltis |
| 2015/0216533 A1 | 8/2015 | Gray et al. |
| 2015/0238734 A1 | 8/2015 | Kanazawa |
| 2015/0290432 A1 | 10/2015 | Matthews |
| 2015/0297863 A1 | 10/2015 | Hannon et al. |
| 2015/0305710 A1 | 10/2015 | Koninklijke |
| 2015/0306355 A1 | 10/2015 | Idstrom |
| 2016/0001048 A1 | 1/2016 | Koike |
| 2016/0008585 A1 | 1/2016 | Tano |
| 2016/0045101 A1 | 2/2016 | Nakatate et al. |
| 2016/0058382 A1 | 3/2016 | Burkett et al. |
| 2016/0089128 A1 | 3/2016 | Weber et al. |
| 2016/0113793 A1 | 4/2016 | Nishigishi |
| 2016/0135827 A1 | 5/2016 | Elsesser |
| 2016/0199620 A1 | 7/2016 | Pokorney |
| 2016/0235337 A1 | 8/2016 | Govari |
| 2016/0361520 A1 | 12/2016 | Braun |
| 2016/0367788 A1 | 12/2016 | Jimenez et al. |
| 2016/0375226 A1 | 12/2016 | Nabeshima |
| 2017/0047740 A1 | 2/2017 | Narla |
| 2017/0136213 A1 | 5/2017 | Kauphusman et al. |
| 2017/0189643 A1 | 7/2017 | Christian |
| 2017/0203076 A1 | 7/2017 | Groneberg et al. |
| 2017/0215954 A1 | 8/2017 | Datta et al. |
| 2017/0234411 A1 | 8/2017 | Dewaele et al. |
| 2017/0281909 A1 | 10/2017 | Northrop et al. |
| 2018/0015260 A1 | 1/2018 | Sano et al. |
| 2018/0015261 A1 | 1/2018 | Lippert |
| 2018/0015262 A1 | 1/2018 | Lippert |
| 2018/0015263 A1 | 1/2018 | Lippert |
| 2018/0028177 A1 | 2/2018 | Van et al. |
| 2018/0071496 A1 | 3/2018 | Snyder |
| 2018/0177517 A1 | 6/2018 | Lippert |
| 2018/0185619 A1 | 7/2018 | Batman et al. |
| 2018/0193603 A1 | 7/2018 | Falb et al. |
| 2018/0193607 A1 | 7/2018 | Lippert |
| 2018/0207407 A1 | 7/2018 | Tanigaki |
| 2019/0008639 A1 | 1/2019 | Landon et al. |
| 2019/0290883 A1 | 9/2019 | Lippert et al. |
| 2020/0016378 A1 | 1/2020 | Williams et al. |
| 2020/0054860 A1 | 2/2020 | Mcelhaney et al. |
| 2020/0094027 A1 | 3/2020 | Davis |
| 2020/0121308 A1 | 4/2020 | Davis et al. |
| 2020/0345975 A1 | 11/2020 | Snyder |
| 2021/0008351 A1 | 1/2021 | Snyder et al. |
| 2021/0162184 A1 | 6/2021 | Lippert et al. |
| 2021/0178128 A1 | 6/2021 | Lippert et al. |
| 2021/0213241 A1 | 7/2021 | Christian et al. |
| 2021/0228845 A1 | 7/2021 | Lippert et al. |
| 2021/0283372 A1 | 9/2021 | Murphy |
| 2021/0283380 A1 | 9/2021 | Lippert et al. |
| 2021/0307766 A1 | 10/2021 | Keating et al. |
| 2021/0346656 A1 | 11/2021 | Lippert et al. |
| 2022/0105312 A1 | 4/2022 | Davis |
| 2022/0105318 A1 | 4/2022 | Davis et al. |
| 2022/0118225 A1 | 4/2022 | Snyder et al. |
| 2022/0280147 A1 | 9/2022 | Davis |
| 2022/0296850 A1 | 9/2022 | Lippert |
| 2023/0071512 A1 | 3/2023 | Maggio et al. |
| 2023/0082226 A1 | 3/2023 | Lippert et al. |
| 2024/0123196 A1 | 4/2024 | Lippert et al. |

FOREIGN PATENT DOCUMENTS

| | | |
|---|---|---|
| AU | 774559 | 7/2004 |
| AU | 2008229892 | 10/2008 |
| BR | 9709363 | 1/2000 |
| BR | 9712829 | 1/2000 |
| CA | 2266685 | 5/2006 |
| CA | 2255781 | 3/2007 |
| CA | 2395149 | 12/2008 |
| CN | 1225282 A | 8/1999 |
| CN | 1230914 | 10/1999 |
| CN | 1324285 | 11/2001 |
| CN | 1422673 | 6/2003 |
| CN | 1518428 | 8/2004 |
| CN | 1781684 | 6/2006 |
| CN | 1897892 A | 1/2007 |
| CN | 101001660 | 7/2007 |
| CN | 101209365 A | 7/2008 |
| CN | 101304778 | 11/2008 |
| CN | 201239164 Y | 5/2009 |
| CN | 101815553 A | 8/2010 |
| CN | 102049085 A | 5/2011 |
| CN | 102107041 A | 6/2011 |
| CN | 102438691 A | 5/2012 |
| CN | 102548603 A | 7/2012 |
| CN | 102639303 A | 8/2012 |
| CN | 102824681 A | 12/2012 |
| CN | 102847225 A | 1/2013 |
| CN | 103301553 A | 9/2013 |
| CN | 103566457 A | 2/2014 |
| CN | 103764012 A | 4/2014 |
| CN | 103799980 A | 5/2014 |
| CN | 103860265 A | 6/2014 |
| CN | 104271035 A | 1/2015 |
| CN | 104302345 A | 1/2015 |
| CN | 104427950 A | 3/2015 |
| CN | 104602616 A | 5/2015 |
| CN | 104602718 A | 5/2015 |
| CN | 104619247 A | 5/2015 |
| CN | 104759022 A | 7/2015 |
| CN | 104812420 A | 7/2015 |
| CN | 105209102 A | 12/2015 |

(56) References Cited

FOREIGN PATENT DOCUMENTS

| | | |
|---|---|---|
| CN | 105228536 A | 1/2016 |
| CN | 105545375 A | 5/2016 |
| CN | 105582611 A | 5/2016 |
| CN | 105682725 A | 6/2016 |
| CN | 105682729 A | 6/2016 |
| CN | 105828690 A | 8/2016 |
| CN | 105979880 A | 9/2016 |
| CN | 107206216 A | 9/2017 |
| DE | 60036882 | 7/2008 |
| DE | 69738235 | 7/2008 |
| EP | 0521595 A2 | 1/1993 |
| EP | 0998323 A1 | 5/2000 |
| EP | 934141 | 11/2005 |
| EP | 921754 | 10/2007 |
| EP | 1239901 | 10/2007 |
| EP | 1844911 A1 | 10/2007 |
| EP | 1940498 | 7/2008 |
| EP | 2964305 | 1/2016 |
| EP | 2414022 B1 | 8/2017 |
| ES | 2293660 | 3/2008 |
| JP | 59102509 | 6/1984 |
| JP | 06-154335 A | 6/1994 |
| JP | 07-008560 | 1/1995 |
| JP | 08-215313 A | 8/1996 |
| JP | 08-243168 A | 9/1996 |
| JP | 08-243169 A | 9/1996 |
| JP | 08-308934 | 11/1996 |
| JP | 11294497 | 10/1999 |
| JP | 2000-503225 A | 3/2000 |
| JP | 2000116787 | 4/2000 |
| JP | 2000-126301 A | 5/2000 |
| JP | 2000511094 | 8/2000 |
| JP | 2000343313 | 12/2000 |
| JP | 2001500808 | 1/2001 |
| JP | 2002543896 | 12/2002 |
| JP | 2003011117 | 1/2003 |
| JP | 2004-025340 A | 1/2004 |
| JP | 2004136121 | 5/2004 |
| JP | 2004329552 | 11/2004 |
| JP | 2004535233 | 11/2004 |
| JP | 2005-514115 A | 5/2005 |
| JP | 2005-534407 A | 11/2005 |
| JP | 2005533594 | 11/2005 |
| JP | 2007-514458 A | 6/2007 |
| JP | 2007313638 | 12/2007 |
| JP | 2008-178656 A | 8/2008 |
| JP | 2008536639 | 9/2008 |
| JP | 2010-029736 A | 2/2010 |
| JP | 2010-503484 A | 2/2010 |
| JP | 2010-535583 A | 11/2010 |
| JP | 2010535588 | 11/2010 |
| JP | 2011-206175 A | 10/2011 |
| JP | 4805208 | 11/2011 |
| JP | 4845313 | 12/2011 |
| JP | 2012-502743 A | 2/2012 |
| JP | 2012-522607 A | 9/2012 |
| JP | 2013-106854 A | 6/2013 |
| JP | 2013-523282 A | 6/2013 |
| JP | 2013-176560 A | 9/2013 |
| JP | 2014-023727 A | 2/2014 |
| JP | 2015-073861 A | 4/2015 |
| JP | 2015-181723 A | 10/2015 |
| JP | 2015-186427 A | 10/2015 |
| JP | 2016-013269 A | 1/2016 |
| JP | 2017-169253 A | 9/2017 |
| KR | 20000015896 | 3/2000 |
| KR | 20000036139 | 6/2000 |
| TW | 412468 | 11/2000 |
| WO | 9419039 | 1/1994 |
| WO | 1994006503 | 3/1994 |
| WO | 97/25914 A1 | 7/1997 |
| WO | 98/58697 A1 | 12/1998 |
| WO | 99/04847 A1 | 2/1999 |
| WO | 9953824 | 10/1999 |
| WO | 2004011076 | 2/2004 |
| WO | 2006/025931 A1 | 3/2006 |
| WO | 2006/058234 A2 | 6/2006 |
| WO | 2006113863 | 10/2006 |
| WO | 2007050718 | 5/2007 |
| WO | 2008/034010 A2 | 3/2008 |
| WO | 2009/020691 A2 | 2/2009 |
| WO | 2009/020836 A1 | 2/2009 |
| WO | 2009020961 | 2/2009 |
| WO | 2009020962 | 2/2009 |
| WO | 2009/143160 A1 | 11/2009 |
| WO | 2010077692 | 7/2010 |
| WO | 2010115163 | 10/2010 |
| WO | 2011/123689 A1 | 10/2011 |
| WO | 2014/005095 A1 | 1/2014 |
| WO | 2014066104 | 5/2014 |
| WO | 2014138580 | 9/2014 |
| WO | 2016047499 | 3/2016 |
| WO | 2016117238 | 7/2016 |
| WO | 2016136609 | 9/2016 |
| WO | 2016152194 | 9/2016 |
| WO | 2016158671 | 10/2016 |
| WO | 2017/151292 A1 | 9/2017 |
| WO | 2018/017349 A1 | 1/2018 |
| WO | 2018/017351 A1 | 1/2018 |
| WO | 2018218216 | 11/2018 |
| WO | 2020/217171 A1 | 10/2020 |
| WO | 2022/159139 A1 | 7/2022 |

OTHER PUBLICATIONS

U.S. Appl. No. 16/281,046, filed Feb. 20, 2019, Snyder.
U.S. Appl. No. 16/439,894, filed Jun. 13, 2019, Lippert.
Canadian Office Action for CA2757655 dated Jan. 2, 2018.
EP10759515.9 Supplementary European Search Report dated Sep. 25, 2012.
European Search Report for EP09836735 dated Nov. 7, 2012.
Supplementary Partial European Search Report for EP14760849 dated Oct. 11, 2016.
European Search Report for EP15197042.3 dated Apr. 11, 2016.
European Search Report for application No. 17184064.8 dated Jan. 5, 2018.
International Search Report and Written Opinion for PCT/US2009/067217 dated Dec. 16, 2010.
International Search Report and Written Opinion for PCT/US2010/029867 dated Jun. 1, 2010.
International Search Report and Written Opinion for PCT/US2014/021742 dated Aug. 27, 2014.
International Search Report and Written Opinion for PCT/US2017/041299 dated Oct. 2, 2017.
International Search Report and Written Opinion for PCT/US2017/041301 dated Oct. 2, 2017.
International Search Report and Written Opinion for PCT/US2017/041305 dated Oct. 2, 2017.
International Search Report and Written Opinion for PCT/US2017/068056 dated Feb. 26, 2018.
International Search Report and Written Opinion for PCT/US2018/034756 dated Aug. 14, 2018.
International Search Report and Written Opinion for PCT/US2019/019046 dated May 17, 2019.
International Search Report and Written Opinion for PCT/US2019/021031 dated Jun. 18, 2019.
International Search Report and Written Opinion for PCT/US2018/034723 dated Sep. 5, 2018.
U.S. Appl. No. 12/633,727, Oct. 16, 2012, Office Action.
U.S. Appl. No. 12/633,727, Feb. 28, 2013, Notice of Allowance.
U.S. Appl. No. 12/753,831, Feb. 1, 2012, Office Action.
U.S. Appl. No. 12/753,831, May 31, 2012, Final Office Action.
U.S. Appl. No. 12/753,831, Mar. 21, 2014, Office Action.
U.S. Appl. No. 12/753,831, Aug. 29, 2014, Final Office Action.
U.S. Appl. No. 12/753,831, Apr. 14, 2015, Notice of Allowance.
U.S. Appl. No. 12/753,836, Dec. 9, 2011, Office Action.
U.S. Appl. No. 12/753,836, May 1, 2012, Final Office Action.
U.S. Appl. No. 12/753,836, Jul. 31, 2014, Office Action.
U.S. Appl. No. 12/753,836, Jan. 9, 2015, Final Office Action.

(56) References Cited

OTHER PUBLICATIONS

U.S. Appl. No. 12/753,836, Jun. 26, 2015, Office Action.
U.S. Appl. No. 12/753,836, Feb. 17, 2016, Final Office Action.
U.S. Appl. No. 12/753,836, Dec. 23, 2016, Office Action.
U.S. Appl. No. 12/753,836, Jul. 14, 2017, Final Office Action.
U.S. Appl. No. 12/753,836, Nov. 24, 2017, Notice of Allowance.
U.S. Appl. No. 12/753,839, Feb. 7, 2012, Office Action.
U.S. Appl. No. 12/753,839, May 31, 2012, Final Office Action.
U.S. Appl. No. 12/753,839, May 5, 2014, Office Action.
U.S. Appl. No. 12/753,842, Aug. 1, 2012, Office Action.
U.S. Appl. No. 12/753,842, Jan. 9, 2013, Final Office Action.
U.S. Appl. No. 12/753,842, Jan. 29, 2014, Office Action.
U.S. Appl. No. 12/753,842, Sep. 4, 2014, Final Office Action.
U.S. Appl. No. 12/753,842, Dec. 29, 2014, Notice of Allowance.
U.S. Appl. No. 12/753,842, Mar. 5, 2015, Notice of Allowance.
U.S. Appl. No. 12/753,849, May 10, 2011, Office Action.
U.S. Appl. No. 12/753,849, Oct. 18, 2011, Office Action.
U.S. Appl. No. 12/753,849, Jun. 6, 2012, Final Office Action.
U.S. Appl. No. 12/753,849, Jan. 3, 2013, Office Action.
U.S. Appl. No. 12/753,849, Oct. 9, 2013, Final Office Action.
U.S. Appl. No. 12/753,849, May 27, 2014, Office Action.
U.S. Appl. No. 12/753,849, Nov. 5, 2014, Interview Summary.
U.S. Appl. No. 12/753,849, Feb. 2, 2015, Notice of Allowance.
U.S. Appl. No. 12/753,849, Apr. 30, 2015, Notice of Allowance.
U.S. Appl. No. 12/753,855, Sep. 15, 2011, Office Action.
U.S. Appl. No. 12/753,855, Apr. 18, 2012, Final Office Action.
U.S. Appl. No. 12/753,855, Feb. 28, 2014, Office Action.
U.S. Appl. No. 12/753,855, Jan. 13, 2015, Final Office Action.
U.S. Appl. No. 12/753,855, May 21, 2015, Office Action.
U.S. Appl. No. 12/753,855, May 5, 2016, Office Action.
U.S. Appl. No. 12/753,855, Nov. 30, 2016, Notice of Allowance.
U.S. Appl. No. 12/753,858, May 10, 2011, Office Action.
U.S. Appl. No. 12/753,858, Oct. 19, 2011, Final Office Action.
U.S. Appl. No. 12/753,858, Feb. 3, 2012, Office Action.
U.S. Appl. No. 12/753,858, Jul. 18, 2012, Final Office Action.
U.S. Appl. No. 12/753,858, Mar. 29, 2013, Office Action.
U.S. Appl. No. 12/753,858, Jan. 17, 2014, Final Office Action.
U.S. Appl. No. 12/753,858, Sep. 4, 2014, Office Action.
U.S. Appl. No. 12/753,858, Nov. 4, 2014, Interview Summary.
U.S. Appl. No. 12/753,858, May 28, 2015, Final Office Action.
U.S. Appl. No. 12/753,858, Dec. 30, 2015, Office Action.
U.S. Appl. No. 12/753,858, Oct. 24, 2016, Office Action.
U.S. Appl. No. 12/753,858, Mar. 27, 2017, Office Action.
U.S. Appl. No. 12/753,858, Oct. 20, 2017, Final Office Action.
U.S. Appl. No. 12/753,858, Mar. 13, 2018, Office Action.
U.S. Appl. No. 12/753,858, Nov. 14, 2018, Final Office Action.
U.S. Appl. No. 12/753,858, Mar. 14, 2019, Notice of Allowance.
U.S. Appl. No. 13/901,375, Dec. 10, 2015, Office Action.
U.S. Appl. No. 13/901,375, Aug. 1, 2016, Office Action.
U.S. Appl. No. 13/901,375, Dec. 27, 2016, Notice of Allowance.
U.S. Appl. No. 14/199,675, Nov. 3, 2016, Office Action.
U.S. Appl. No. 14/199,675, May 18, 2017, Final Office Action.
U.S. Appl. No. 14/199,675, Sep. 6, 2017, Notice of Allowance.
U.S. Appl. No. 15/465,399, Apr. 23, 2018, Office Action.
U.S. Appl. No. 15/465,399, Sep. 10, 2018, Notice of Allowance.
U.S. Appl. No. 15/611,328, Mar. 27, 2019, Office Action.
U.S. Appl. No. 15/611,344, Mar. 26, 2019, Office Action.
U.S. Appl. No. 15/606,607, May 14, 2019, Office Action.
U.S. Appl. No. 15/611,328, Sep. 24, 2019, Final Office Action.
U.S. Appl. No. 15/848,878, Oct. 29, 2019, Office Action.
U.S. Appl. No. 15/611,344, Nov. 12, 2019, Final Office Action.
U.S. Appl. No. 15/606,607, Nov. 19, 2019, Final Office Action.
U.S. Appl. No. 15/698,553, Nov. 27, 2019, Office Action.
U.S. Appl. No. 15/848,878, Feb. 5, 2020, Office Action.
U.S. Appl. No. 16/212,425, Mar. 16, 2020, Office Action.
International Search Report and Written Opinion for Application PCT/US2017/050602 dated Nov. 7, 2017.
International Search Report and Written Opinion received for PCT Patent Application No. PCT/US2020/030589, dated Jul. 17, 2020, 7 pages.
International Search Report and Written Opinion, PCT App. No. PCT/US2020/013754, dated Jun. 9, 2020, 11 pages.
Non-Final Office Action received for U.S. Appl. No. 15/606,607, dated Jun. 10, 2020, 26 pages.
Final Office Action received for U.S. Appl. No. 16/212,425, dated Aug. 3, 2020, 14 pages.
Final Office Action received for U.S. Appl. No. 15/848,878, dated Aug. 27, 2020, 13 pages.
Non-Final Office Action received for U.S. Appl. No. 15/611,328, dated Jun. 29, 2020, 13 pages.
Non-Final Office Action received for U.S. Appl. No. 15/917,255, dated Aug. 17, 2020, 12 pages.
U.S. Appl. No. 15/698,553, May 15, 2020, Notice of Allowance.
U.S. Appl. No. 15/611,344, May 21, 2020, Office Action.
Non-Final Office Action received for U.S. Appl. No. 16/281,046, dated Oct. 29, 2020, 18 pages.
Final Rejection received for U.S. Appl. No. 15/606,607, dated Dec. 15, 2020, 24 pages.
Final Office Action received for U.S. Appl. No. 16/281,046, dated May 11, 2021, 18 pages.
International Search Report and Written Opinion received for PCT Patent Application No. PCT/US21/14656, dated Apr. 28, 2021, 8 pages.
Non-Final Office Action received for U.S. Appl. No. 15/848,878, dated Jun. 3, 2021, 13 pages.
Final Office Action received for U.S. Appl. No. 16/616,220, dated Oct. 12, 2022, 17 pages.
Non-Final Office Action received for U.S. Appl. No. 17/177,782, dated Nov. 4, 2022, 7 pages.
Final Office Action received for U.S. Appl. No. 15/848,878, dated Sep. 22, 2021, 12 pages.
Final Office Action received for U.S. Appl. No. 17/216,127, dated Jun. 13, 2022, 8 pages.
International Search Report and Written Opinion received for PCT Patent Application No. PCT/US21/042753, dated Nov. 5, 2021, 14 pages.
Non-Final Office Action received for U.S. Appl. No. 16/616,139, dated Oct. 26, 2021, 11 pages.
Non-Final Office Action received for U.S. Appl. No. 16/616,220, dated Jun. 3, 2022, 20 pages.
Non-Final Office Action received for U.S. Appl. No. 16/855,366, dated Jul. 11, 2022, 13 pages.
Non-Final Office Action received for U.S. Appl. No. 16/855,366, dated Jun. 23, 2021, 15 pages.
Final Office Action received for U.S. Appl. No. 16/855,366, dated Dec. 8, 2022, 18 pages.
Non-Final Office Action received for U.S. Appl. No. 17/177,782, dated Jan. 23, 2023, 14 pages.
International Search Report and Written Opinion received for PCT Patent Application No. PCT/US22/42514, dated Dec. 28, 2022, 11 pages.
International Search Report and Written Opinion received for PCT Patent Application No. PCT/US22/42517, dated Feb. 7, 2023, 11 pages.
International Search Report and Written Opinion received for PCT Patent Application No. PCT/US2021/053647, dated Dec. 28, 2021, 9 pages.
International Search Report and Written Opinion received for PCT Patent Application No. PCT/US2021/053652, dated Dec. 28, 2021, 9 pages.
Non-Final Office Action received for U.S. Appl. No. 17/036,302, dated Mar. 1, 2023, 29 pages.
Strength of Materials/Torsion, Wikibooks, 3 pp., accessed Feb. 22, 2023 (en.wikibooks.org/wiki/Strength_of_Materials/Torsion) (last edited Feb. 1, 2022) (Year: 2022).
Chinese Search Report for Chinese Application No. 201780070242. X, dated Sep. 14, 2016, 4 pages.
InternationalSearch Report and Written Opinion for application PCT/US2017/050802 dated Nov. 7, 2017.
Final Office Action received for U.S. Appl. No. 17/154,777, mailed on Apr. 17, 2024, 17 pages.

* cited by examiner

GUIDEWIRE WITH CORE CENTERING MECHANISM

CROSS-REFERENCE TO RELATED APPLICATIONS

This application claims priority to and the benefit of U.S. Provisional Patent Application Ser. No. 62/792,775, filed Jan. 15, 2019 and titled "Guidewire with Core Centering Mechanism," the entirety of which is incorporated herein by this reference.

BACKGROUND

Guidewire devices are often used to lead or guide catheters or other interventional devices to a targeted anatomical location within a patient's body. Typically, guidewires are passed into and through a patient's vasculature in order to reach the target location, which may be at or near the patient's heart or brain, for example. Radiographic imaging is typically utilized to assist in navigating a guidewire to the targeted location. In many instances, a guidewire is placed within the body during the interventional procedure where it can be used to guide multiple catheters or other interventional devices to the targeted anatomical location.

Guidewires are available with various outer diameter sizes. Widely utilized sizes include 0.014, 0.016, 0.018, 0.024, and 0.035 inches, for example, though they may also be smaller or larger in diameter. Because torque transmission is a function of diameter, larger diameter guidewires typically have greater torque transmission (the ability to effectively transfer torque from proximal portions of the wire to more distal portions of the wire). On the other hand, smaller diameter guidewires typically have greater flexibility.

Some guidewires are constructed with a core and an outer tube that surrounds the distal portion of the core. The core is often formed of a relatively stiff material such as stainless steel while the outer member is often formed from a more flexible material such as nitinol. The outer member may also include machined transverse slots to increase flexibility. The intent behind such designs is to reduce the diameter of the core in the distal sections of the guidewire in order to increase the flexibility of the wire, while utilizing the larger outer diameter of the outer member for effective torque transmission.

While such guidewires have seen success, several limitations remain. In particular, the difference in diameter between the outer tube and the core creates an annular space within the coincident sections of the guidewire. Because the outer tube is by design more elastic than the core wire, as the wire navigates a bend, the core will be positioned off-center from the center line of the outer tube. As the guidewire is moved through the vasculature, this off-centering can disrupt the smooth distal transmission of rotational movement, causing a buildup and sudden release of forces which lead the guidewire to move with a "snap" and/or "whip" to a preferential rotational location. This disruption to the tactile feel and control of the guidewire can make it more difficult for the operator to rotationally position the guidewire as intended, raising the risk of interventional procedure delays, suboptimal outcomes, inability to access the target location, or even tissue injury.

BRIEF SUMMARY

The present disclosure relates to intravascular devices such as guidewires having a core disposed within an outer tube and including one or more centering mechanisms configured to assist in radially centering the core within the outer tube. The one or more centering mechanisms beneficially reduce undesirable whip and/or snap movements of the guidewire (i.e., the centering mechanisms may improve rotational control), thereby enabling a user to have greater control and improved tactile handling of the guidewire.

In one embodiment, a guidewire device includes a core having a proximal section and a tapered distal section. An outer tube is coupled to the core such that the tapered distal section of the core extends into and is surrounded by the outer tube. The outer tube may include a plurality of fenestrations to increase the flexibility of the outer tube. One or more centering mechanisms are positioned within at least a portion of the annular space between the core and the outer tube to assist in maintaining axial alignment of the core within the tube. Unlike a simple joint or adhesive plug, the centering mechanism(s) are positioned to extend along at least 15% of the length of the outer tube and optionally up to the full length of the outer tube, such as about 15% to 100% of the length of the outer tube. Preferred embodiments include one or more centering mechanisms that extend along at least about 30%, at least about 40%, at least about 50%, at least about 60%, at least about 70%, at least about 80%, or at least about 90% of the length of the outer tube.

In some embodiments, the core is formed from stainless steel, and the tube is formed from a superelastic material such as nitinol, though other suitable biocompatible materials may additionally or alternatively be used. Some embodiments further include a marker coil positioned between an outer surface of a distal section of the core and an inner surface of the outer tube. The coil may be formed from a radiopaque material.

In some embodiments, a centering mechanism includes one or more centering coils disposed within the annular space. The centering coil may be formed from a suitable metal or metal alloy, such as nitinol or stainless steel, or alternatively may be formed from a suitable polymer as described below. A centering coil as used herein is sized to fit within and fill a portion of the annular space. That is, the centering coil has an outer diameter equal to or less than an inner diameter of the tube and has an inner diameter greater than or equal to the outer diameter of the core, marker coil, and/or other component of the core wire assembly.

Other embodiments may additionally or alternatively include different centering mechanisms, such as a polymer filler and/or an inner tube. A polymer filler is preferably a soft material that structurally fills the annular space with minimal effects on the bending flexibility profile of the device. An inner tube may likewise structurally fill a portion of the annular space to provide centering effects. Preferably, for a majority of the length of the components, the flexibility profile of the inner tube is substantially matched to or is less than the flexibility profile of the outer tube.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

A more particular description of the invention briefly described above will be rendered by reference to specific embodiments which are illustrated in the appended drawings. Understanding that these drawings depict only typical embodiments of the invention and are not limiting of its scope, the invention will be described and explained with additional specificity and detail through the use of the accompanying drawings in which.

DETAILED DESCRIPTION

Figure 1:
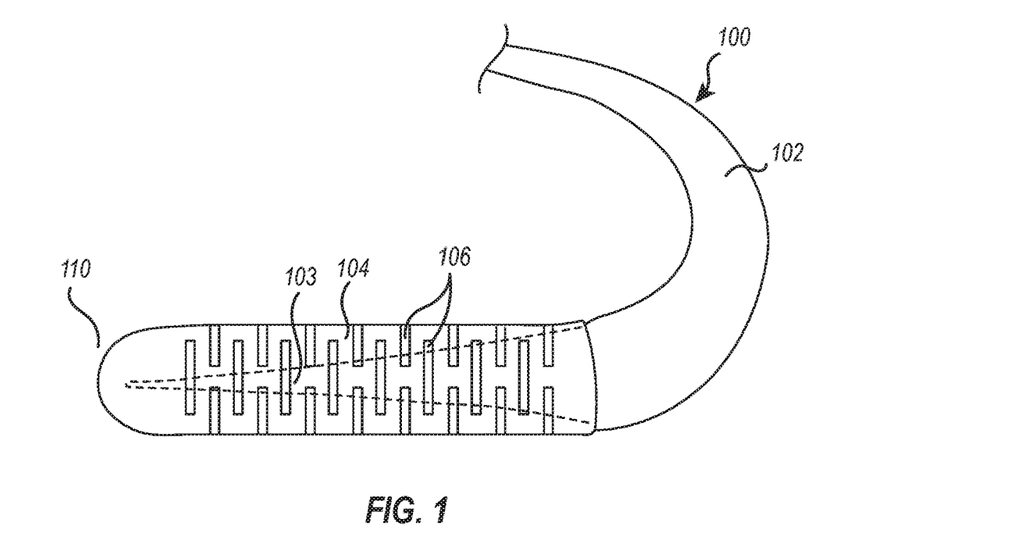
FIG. 1 illustrates an embodiment of a guidewire device having a core and an outer tube and which may utilize one or more of the core centering mechanisms described herein.

FIG. 1 schematically illustrates a guidewire 100 that may utilize one or more features of the present disclosure. The illustrated guidewire 100 includes a core 102 and an outer tube 104. The core 102 includes a distal section (referred to herein as distal core 103) that extends into the outer tube 104 as shown. The distal core 103 may be tapered, either continuously or in one or more discrete sections, so that the more distal sections have a smaller diameter and greater flexibility than more proximal sections. In some embodiments, the most distal section of the core 102 may be flattened into a ribbon-like shape with a flat, rectangular, or oblong cross section. For example, the distal core 103 may be ground so as to progressively taper to a smaller diameter at the distal end.

The core 102 and the tube 104 are typically formed from different materials. For example, the tube 104 is preferably formed from a relatively flexible and elastic material such as nitinol, whereas the core 102 may be formed from a relatively less flexible and elastic material such as stainless steel. Forming the core 102 from stainless steel may be advantageous because it allows the distal tip to hold a shape when selectively bent/shaped by an operator and because stainless steel provides sufficient modulus of elasticity to provide more responsive translational movement. While these materials are presently preferred, other suitable materials such as polymers or other metals/alloys may also be utilized.

In the illustrated device, the core 102 outer diameter and the tube 104 inner diameter have substantially similar diameters at the attachment point where the core 102 enters the tube 104. In some embodiments, the core 102 outer diameter and the tube 104 inner diameter have different diameters at the attachment point, with the difference in diameter being compensated for by a weld, solder, adhesive, or other means of structural attachment, or by positioning a portion of a centering mechanism (e.g., centering coil, braid, or tube) at the attachment point and/or through the use of another bushing structure. The tube 104 is coupled to the core 102 (e.g., using adhesive, soldering, and/or welding) in a manner that beneficially allows torsional forces to be transmitted from the core 102 to the tube 104 and thereby to be further transmitted distally by the tube 104. A medical grade adhesive or other suitable material may be used to couple the tube 104 to the core wire 102 at the distal end 110 of the device to form an atraumatic covering.

The outer tube 104 may include a cut pattern that forms fenestrations 106 in the tube. The pattern of fenestrations 106 may be arranged to provide desired flexibility characteristics to the tube 104, including the promotion of preferred bending directions, the reduction or elimination of preferred bending directions, or gradient increases in flexibility along the longitudinal axis, for example. Examples of cut patterns and other guidewire device features that may be utilized in the guidewire devices described herein are provided in detail in United States Patent Application Publication Nos. 2018/0193607 and 2018/0071496, and in Patent Cooperation Treaty Application No. PCT/US2018/034756, the entireties of each of which are incorporated herein by this reference.

The proximal section of the guidewire device 100 (the portion extending proximally from the tube 104) extends proximally to a length necessary to provide sufficient guidewire length for delivery to a targeted anatomical area. The guidewire device 100 typically has a length ranging from about 50 cm to about 350 cm depending on particular application needs. The tube 104 may have a length ranging from about 20 cm to about 65 cm, more typically about 30 cm to about 55 cm such as about 35 cm to about 45 cm.

The guidewire device 100 may have a diameter of about 0.014 inches to about 0.035 inches, though larger or smaller sizes may also be utilized depending on particular application needs. For example, particular embodiments may have outer diameter sizes corresponding to standard guidewire sizes such as 0.014 inches, 0.016 inches, 0.018 inches, 0.024 inches, or other such sizes common to guidewire devices. The distal section 103 of the core 102 may taper to a diameter of about 0.002 inches, or a diameter within a range of about 0.001 to 0.005 inches. In some embodiments, the distal tip may be flattened (e.g., to a rectangular cross section) to further enhance bending flexibility while minimizing reductions in cross-sectional area needed for tensile strength. In such embodiments, the cross section may have dimensions of about 0.001 inches by 0.003 inches, for example. In some embodiments, the tube 104 has a length within a range of about 3 to 100 cm.

Figure 2A:
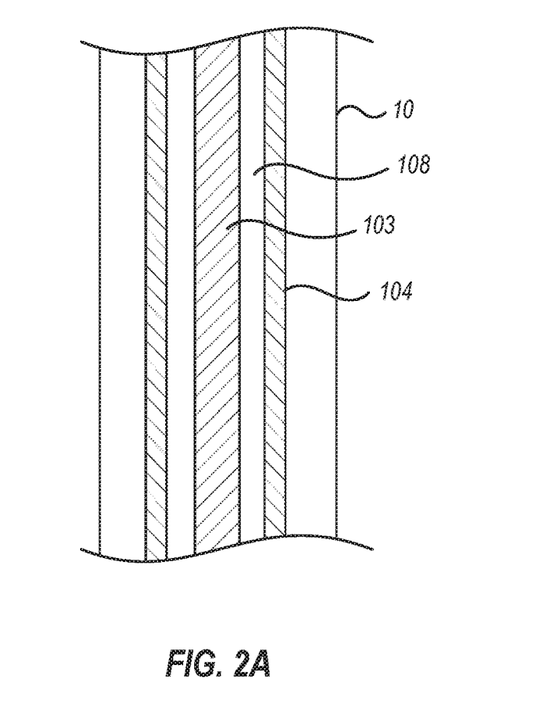
FIGS. 2A and 2B illustrate a cross section of a vessel in which a guidewire has been inserted, with FIG. 2A showing a straight section of the vessel and FIG. 2B showing a curved section of the vessel where the core tends to move out of axial alignment with the outer tube.
Figure 2B:
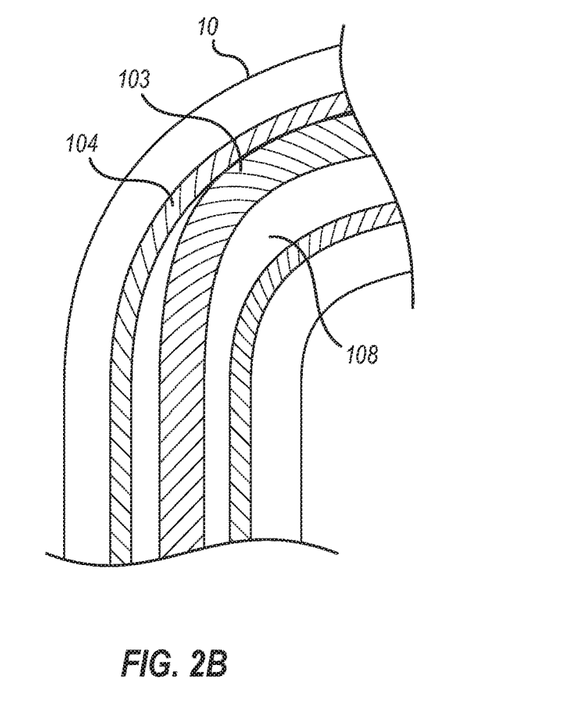

FIGS. 2A and 2B show a cross-sectional view of a vessel 10 in which the distal portion of the guidewire device 100 has been inserted. As shown in FIG. 2A, in relatively straighter sections of the vessel 10, the outer tube 104 and the distal core 103 may be essentially radially centered. An annular space 108 exists within the tube 104 between the inner surface of the tube 104 and the outer surface of the distal core 103. FIG. 2B shows a curved section of the vessel 10 illustrating one example of how the distal core 103 may become off-center relative to the outer tube 104. As the guidewire curves to match the curvature of the vessel 10, the relatively less flexible distal core 103 will not bend as readily as the coincident section of the outer tube 104. This causes the distal core 103 to move off center within the tube 104. This misalignment can disrupt smooth rotational movement, causing a buildup and sudden release of energy which leads the guidewire to undesirably "snap" and/or "whip".

Problems associated with off-centered alignment of the core may be more problematic as guidewire size goes up. As guidewire size goes up, the inner diameter of the tube 104 may increase more than the outer diameter of the distal core 103. That is, the diameter of the tube 104 may be increased to give greater torquability but the diameter of the distal core 103 may be substantially maintained to preserve the flexibility profile of the distal portion of the device. This means that larger sized guidewires will often have larger annular spaces 108 and are therefore more prone to misalignment of the core relative to the longitudinal axis of the tube 104. By way of example, where a 0.014 inch guidewire device may in some circumstances function adequately without any core centering mechanism, a larger sized guidewire such as a 0.018 or 0.024 inch guidewire may increasingly exhibit problems associated with core off-centered alignment. In other circumstances, however, the core centering mechanisms described herein may be beneficially used even in smaller guidewires such as a 0.014 inch guidewire.

FIGS. 3 through 12 illustrate various exemplary embodiments of guidewire devices including core centering features configured to reduce or eliminate the undesirable misalignment described above. Some embodiments may incorporate and combine components from one or more of the disclosed embodiments. The following embodiments may incorporate features of the guidewire device 100 described above, and are presented herein to more particularly illustrate exemplary core centering mechanisms. Further, it will be understood that while the illustrated embodiments are described in the context of guidewire devices, the same concepts and features may also be utilized in other intravascular devices, such as intravascular catheters including an outer tube and an inner member where enhanced centering of the inner member would be beneficial.

Figure 3:
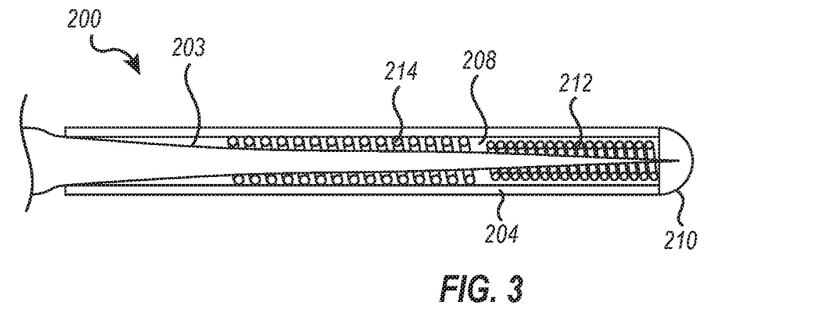
FIG. 3 illustrates an embodiment of a guidewire device including a centering coil disposed within an annular space between the core and an inner surface of the outer tube.

FIG. 3 illustrates a distal section of a guidewire 200 having a core 203 disposed within an outer tube 204. The guidewire 200 includes a distal marker coil 212 formed from one or more radiopaque materials, such as platinum group, gold, silver, palladium, iridium, osmium, tantalum, tungsten, bismuth, dysprosium, gadolinium, and the like. The marker coil 212 allows radiographic visualization of the distal end of the guidewire 200 during a procedure. In the illustrated embodiment, the marker coil 212 is disposed at or near the distal end 210 of the device and extends a distance proximally. In some embodiments, the marker coil 212 has a length that substantially coincides with the length of the tube 204, though in typical embodiments the marker coil 212 is shorter than the tube 204. For example, the marker coil 212 may have a length of about 1 to 30 cm, or more typically about 3 to 15 cm, such as about 5 to 10 cm.

As illustrated, the guidewire 200 includes an annular space 208 between the core 203 and the tube 204. A centering coil 214 is provided within the annular space 208 to fill the annular space and limit radial movement of the core 203 relative to the tube 204. This aids in maintaining centering of the core 203 within the tube 204, which prevents the undesirable effects of misalignment that have been described above while also minimally impacting the bending flexibility of the device. Although the centering coil examples illustrated herein are shown having wires with a circular cross section, it will be understood that other coil types may also be utilized. For example, centering coil(s) may be edge-wound and/or may have a ribbon, rectangular, oblong, or other non-circular shaped cross-sectional shape.

The centering coil 214 is separate from the marker coil 212. In theory, the marker coil 212 could be extended and/or enlarged to fill more of the annular space 208 and thereby serve a centering function. However, materials that function well as radiopaque markers (e.g., platinum) are relatively expensive. Also, their use as a packing material to fill large portions of the annular space 208 could cause the distal section of the guidewire 200 to be overly bright when imaged under x-ray fluoroscopy and thus not allow the operator to visualize other areas of interest. Although a small gap may be shown between the marker coil 212 and the centering coil 214, other embodiments may position the respective coils so as to be in contact with one another or substantially adjacent to one another (see, e.g., FIG. 7).

The centering coil 214 may be formed from a suitable metal or metal alloy, such as nitinol or stainless steel. Although stainless steel is capable of taking a set, when it is provided in the form of a coil it eliminates or vastly reduces its propensity to do so. The centering coil 214 is configured to maintain sufficient flexibility to minimize disruption to the overall flexibility of the coincident portions of the guidewire 200. The benefits resulting from enhanced centering of the core 203 have also been found to outweigh any changes in the overall flexibility profile of the device, particularly in guidewires larger than 0.014 inches.

The centering coil 214 may be alternatively be formed from one or more polymer materials. In some embodiments, for example, the centering coil may be formed from a polymer such as nylon, polypropylene, polyethylene, acetal copolymer, polyphenylene sulfide, acrylonitrile butadiene styrene (ABS), and/or other suitable polymers.

The centering coil 214 preferably extends along a substantial portion of the length of the tube 204. For example, the centering coil 214 preferably has a length of at least about 15% of the length of the tube 204, or at least about 20%, 30%, 40%, 50%, 60%, 70%, 80%, 90%, or even 100% of the length of the tube 204, or a length within a range with endpoints defined by any two of the foregoing values. In some embodiments, a centering coil may extend beyond the proximal and/or distal end of the tube 204 and thus may be longer than the tube 204. Providing the centering coil 214 with adequate length within the tube 204 ensures the presence of enough structure to enable sufficient centering of the core 203.

The centering coil 214 is sized to fit within and fill a portion of the annular space 208. That is, the centering coil 214 has an outer diameter equal or less than an inner diameter of the tube 204 and an inner diameter greater than or equal to the outer diameter of the core 203. Of course, in certain embodiments the core 203 will taper and the outer diameter of the core 203 will vary according to longitudinal position. In such embodiments, the inner diameter of the centering coil 214 will dictate where the centering coil 214 may be positioned due to the allowable amount of interstitial space.

The structural properties of the centering coil 214 may relate to positioning of the centering coil 214 within the annular space 208. For example, if the proximal end of the centering coil 214 is located too far distally, the centering coil 214 may not coincide with a sufficient length of the tube 204 to effectively provide centering. On the other hand, if the proximal end of the centering coil is located too far proximally, at a location where the diameter of the core 203 is larger, the inner diameter of the centering coil 214 may be too large to allow the centering coil 214 to fill much of the annular space 208. For some embodiments, a good balance has been found when the proximal end of the centering coil 214 is located at a point where the diameter of the core 203 is approximately 20 to 80% of the inner diameter of the tube 204. These values may be adjusted according to particular design features such as the particular tapering profile of the core 203, the number of centering coils utilized, and particular application needs. Preferably, core centering mechanism(s) such as centering coil 214 are provided so as to take up as much annular space as possible while minimizing increases in bending flexibility. As explained in more detail below, some embodiments may therefore utilize one or more additional centering coils and/or one or more alternative features (such as a braid, tube, polymer filler, set of stacked rings, coil with a tapering inner diameter, or microfabricated tube) to fill the annular space and provide centering.

The centering coil 214 may be positioned so as to avoid overlap with the marker coil 212, as shown in FIG. 3. Alternatively, a portion of the centering coil 214 can extend over the marker coil 212, provided that the inner diameter of the centering coil 214 is equal to or larger than the outer diameter of the marker coil 212.

In some embodiments, a single centering coil 214 is sufficient to provide effective centering of the core 203. However, as described in more detail below, additional centering mechanisms may also be provided to enhance the overall centering effect of the device. By way of example, given a core that tapers to a diameter of approximately 0.001 to 0.006 inches (e.g., about 0.002 inches), or that tapers to a flat shape, the single centering coil embodiment illustrated in FIG. 3 has been found to be effective when the guidewire 200 is sized from about 0.014 inches to about 0.024 inches, such as where the guidewire 200 is about 0.018 inches (with the size being determined by the outer diameter of the tube 204 and/or section of the core proximal of the tube 204).

Figure 4:
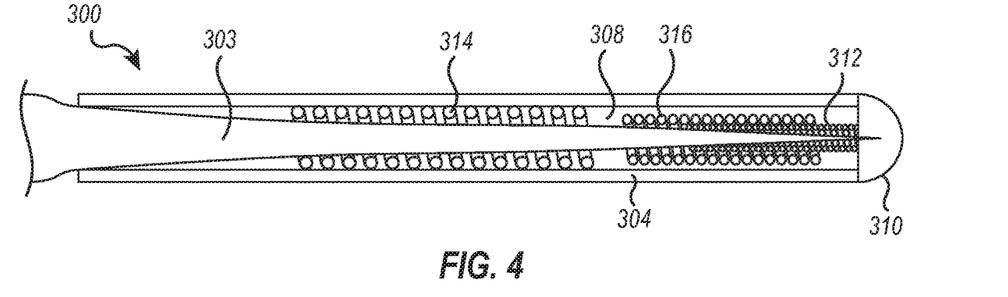
FIG. 4 illustrates another embodiment of a guidewire device including multiple centering coils disposed within the annular space.

FIG. 4 illustrates an alternative embodiment of a guidewire 300 including multiple centering coils. Multiple centering coils may be advantageous for filling additional annular space 308 and promoting additional centering of the core 303, such as for larger sized guidewires. By way of example, given a core that tapers to a diameter of approximately 0.001 to 0.006 inches (e.g., about 0.002 inches), or that tapers to a flat shape, the multiple centering coil embodiment illustrated in FIG. 4 has been found to be effective when the guidewire 300 is sized from about 0.018 inches to about 0.035 inches, such as where the guidewire 300 is about 0.024 inches. The guidewire 300 is otherwise similar to the guidewire 200 and except where noted the description of guidewire components of FIG. 3 may be applied to similar components of the guidewire 300 of FIG. 4.

The guidewire 300 includes a first centering coil 314 disposed proximal of a more distal (i.e., closer to distal end 310), second centering coil 316. Other embodiments may include more than two centering coils, such as three, four, five, or more. The second centering coil 316 may at least partially extend over the marker coil 312, as shown, or may be positioned so that the full length of the second centering coil 316 coincides with at least a portion of the marker coil 312.

Multiple coils may be used advantageously to better match the tapering profile of the core 303 and more effectively fill the annular space 308 of the tube 304. For example, centering coils positioned more proximally may have larger inner diameters because of the larger diameters of the corresponding proximal sections of the core 303, whereas centering coils positioned at progressively distal locations may have progressively smaller inner diameters to better match the correspondingly smaller diameters of the more distal sections of the core 303. Of course, where a centering coil such as coil 316 overlaps with the marking coil 312, the centering coil 316 inner diameter will be sized accordingly to allow the overlap.

In embodiments with multiple centering coils, the centering coils with relatively smaller inner diameters may be formed from larger wire sizes to compensate and provide structure to fill the annular space 308. Stated differently, the ratio of the outside diameter to the inside diameter (OD/ID) of a first centering coil may be different than that of one or more other centering coils. Typically, the more distal the centering coil is positioned the higher the OD/ID will be relative to other centering coils in the device. This is because the more distally located centering coils will be located at sections of the core 303 with smaller core diameter, and these centering coils will therefore have smaller inner diameters with larger wire sizes. A distal centering coil disposed over the marker coil 312 will not follow this same trend, however, since its inner diameter must account for the marker coil 312 and not just the underlying core 303.

Centering coils such as those shown in FIGS. 3 and 4 may be bonded to the core at desired positions by soldering, welding, adhesive bonding, or other suitable fastening means. Alternatively, if the tube is bonded at both ends to the core, the annular space will be essentially closed, and the centering coil(s) may be simply positioned within the tube and allowed to "float" without being fastened directly to the core or tube.

Further, centering coils such as those shown in FIGS. 3 and 4 preferably have a pitch that allows sufficient bending but minimizes increases in bending stiffness. A larger pitch provides more room for bending before adjacent coils on the inside of the bend become stacked against each other. However, a larger pitch also means each turn of the coil will have a larger axial component adding to the bending stiffness of the device. In some embodiments, the centering coil may be essentially stacked (i.e., the pitch equals the coil wire diameter). In preferred embodiments, however, the centering coil has a pitch slightly greater than the coil wire diameter. The ratio of the pitch of a centering coil to the coil wire diameter may be about 1.05 to about 2, or about 1.075 to about 1.5, or more preferably about 1.1 to 1.3. For example, the coil wire diameter may be about 0.009 inches, and the pitch may be about 0.01 inches. In embodiments where the coil wire has a non-circular cross section, the coil wire "diameter" corresponds to the longitudinal/axial dimension of the coil wire when positioned within the annular space.

Figure 5:
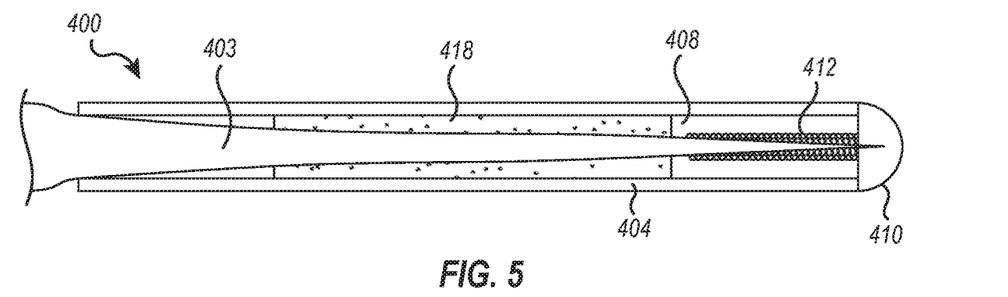
FIG. 5 illustrates another embodiment of a guidewire device including a polymer filler disposed within the annular space.

FIG. 5 illustrates another embodiment of a guidewire 400 having a core centering mechanism. Rather than a centering coil, guidewire 400 includes a polymer filler 418 disposed within at least a portion of the annular space 408 between core 403 and tube 404. The guidewire 400 may otherwise include components described in relation to other embodiments described herein, including a marker coil 412 disposed at or near the distal end 410 of the guidewire device 400. The polymer filler 418 functions similar to the centering coil(s) of other embodiments by filling at least a portion of the annular space 408 and assisting in maintaining radial centering of the core 403 within the tube 404. The polymer filler 418 need not function as or be utilized as an adhesive to join anything to the core 403. Rather, the polymer filler 418 functions as a core centering mechanism while minimally adding to the overall bending stiffness of the device.

The polymer filler 418 may be a polymer tube, a polymer foam, a polymer wrap, or other structure capable of being held within the annular space. The polymer tube may include a cut pattern that forms fenestrations in the tube. In some embodiments, the polymer filler 418 may be wrapped, dipped, extruded and ground, or otherwise applied to the core 403 so that the inner diameter of the polymer filler 418 substantially conforms to the core 403. If necessary, the outer diameter of the polymer filler 418 may be ground or otherwise machined to a proper size to allow the tube 404 to be positioned over the polymer filler 418.

The polymer filler 418 is preferably a soft material such as an elastomer that structurally fills the annular space 408 with minimal effects on the bending flexibility profile of the device. The filler material 418 may comprise, for example, urethane, polyisoprene (e.g., natural rubber), polybutadiene (BR), chloroprene (CR), butyl rubber (IIR), styrene-butadiene (SBR), nitrile rubber (NBR), ethylene propylene rubber (EPM), ethylene propylene diene rubber (EPDM), epichlorohydrin rubber (ECO), polyacrylic rubber (ACM, ABR), silicone rubber(s), fluoroelastomer(s), polyether block amides (PEBA), chlorosulfonated polyethylene (CSM), ethylene-vinyl acetate (EVA), and combinations thereof. In some embodiments, at least a portion of the polymer (e.g., the distal portion) may be doped with one or more materials such as bismuth, tungsten, barium sulphate, and/or other radiopaque materials to increase radiopacity of the polymer. Such embodiments may eliminate the need for a marker coil. The polymer filler 418 preferably has a durometer of about 10 to 90 Shore A.

The polymer filler material 418 may fill a proportion of the annular space 408 similar to a proportion filled by centering coil(s) in other embodiments. For example, the polymer filler 418 may fill at least about 15% of the length of the tube 404, or at least about 20%, 30%, 40%, 50%, 60%, 70%, 80%, 90%, or even 100% of the length of the tube 404, or a length within a range with endpoints defined by any two of the foregoing values.

The polymer filler 418 may be combined with one or more centering coils such as shown in other embodiments. For example, some guidewire embodiments may fill one or more sections of the annular space with a filler material and one or more other sections of the annular space with a centering coil. Such embodiments may position the filler material at more proximal sections within the tube where any resulting degradation to the bending flexibility of the device is somewhat less critical and the centering coil(s) at more distal sections within the tube where flexibility requirements are more sensitive, though this arrangement is not necessary.

Figure 6:
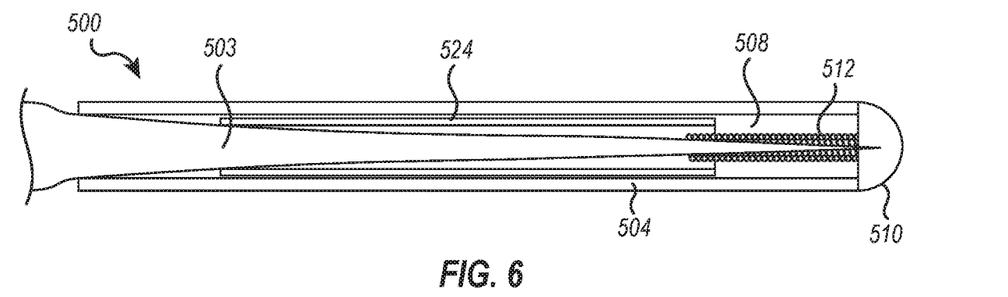
FIG. 6 illustrates another embodiment of a guidewire device including an inner tube disposed within the annular space.

FIG. 6 illustrates another embodiment of a guidewire 500 that includes an inner tube 524 disposed within the annular space 508 between the core 503 and the tube 504 to function as a centering mechanism. The guidewire 500 may otherwise include components similar to other embodiments described herein, including a marker coil 512 disposed at or near the distal end 510 of the guidewire device 500. The inner tube 524 functions similar to the centering coil(s) or polymer filler of other embodiments by packing at least a portion of the annular space 508 and thereby assisting in maintaining radial centering of the core 503 within the tube 504.

The inner tube 524 may be similar to the outer tube 504 apart from its smaller diameter and length. For example, the inner tube 524 may be formed from a flexible material such as nitinol, and preferably includes flexibility-increasing fenestrations according to one or more cut patterns referenced above. In some embodiments, the flexibility profile of the outer tube 504 is substantially matched to the flexibility profile of the inner tube 524. For example, where the outer tube 504 includes a gradient flexibility profile as a result of the arrangement of fenestrations (e.g., greater density, depth, and/or size of fenestrations at more distal sections), the inner tube 524 may be configured so that the flexibility of the outer tube 504 and inner tube 524 match for a given length of the device.

The inner tube 524 may fill a proportion of the annular space 508 similar to a proportion filled by centering coil(s) in other embodiments. For example, the inner tube 524 may fill at least about 15% of the length of the tube 504, or at least about 20%, 30%, 40%, 50%, 60%, 70%, 80%, 90%, or even 100% of the length of the tube 504, or a length within a range with endpoints defined by any two of the foregoing values.

The inner tube 524 may be combined with one or more centering coils and/or polymer fillers such as shown in other embodiments. For example, some guidewire embodiments may fill one or more sections of the annular space with an inner tube and one or more other sections of the annular space with a centering coil and/or polymer filler.

Figure 7:
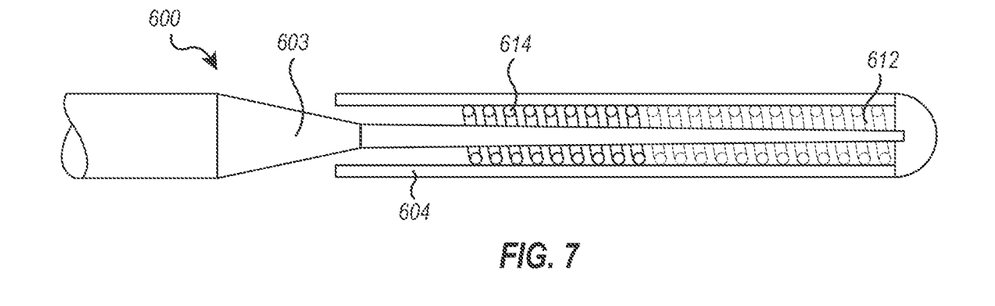
FIG. 7 illustrates another embodiment of a guidewire device including a centering coil positioned adjacent to a marker coil within an annular space.

FIG. 7 illustrates another embodiment of a guidewire 600 including a single centering coil 614 positioned adjacent to a marker coil 612 within the annular space between the core 603 and the tube 604. Guidewire 600 may be similar to guidewire 200 of FIG. 3, and the description of the components of FIG. 3 may therefore be applied to similar components of FIG. 7. Guidewire 600 illustrates that the centering coil 614 and marker coil 612 may be essentially contacted against each other to minimize any gap between the separate coils. As in embodiments described above, the marker coil 612 may be formed from a radiopaque material such as platinum, while the separate centering coil 614 is formed from a different (e.g., less expensive) material such as stainless steel, other suitable, metal, or a suitable polymer material.

Figure 8:
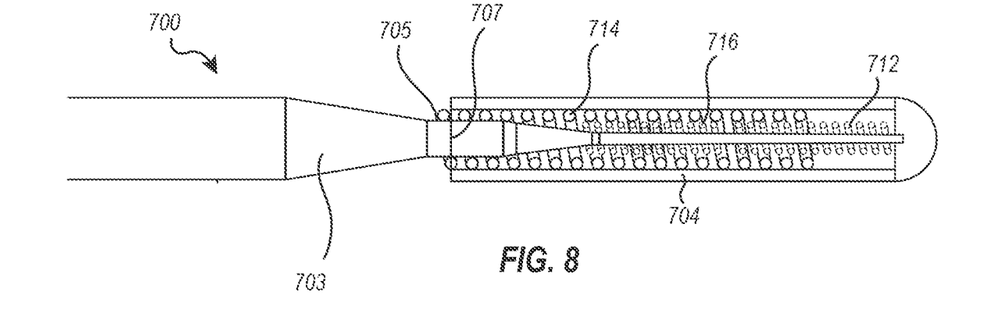
FIG. 8 illustrates another embodiment of a guidewire device including multiple centering coils and showing that a proximal centering coil may be extended proximally beyond the outer tube.

FIG. 8 illustrates another embodiment of a guidewire 700 having multiple centering coils (714 and 716) positioned within the annular space between the core 703 and the tube 704. Guidewire 700 may be similar to guidewire 300 of FIG. 4, and the description of the components of FIG. 4 may therefore be applied to similar components of FIG. 8. Guidewire 700 illustrates an alternative arrangement of centering coils in which a first centering coil 714 overlaps and extends over at least a portion of a second centering coil 716. As shown, the first centering coil 714 may also overlap and extend over at least a portion of the marker coil 712. The second centering coil 716 may be positioned proximal of the centering coil 712, and may extend proximally until reaching a portion of the core 703 where the outer diameter of the core 703 matches the inner diameter of the second centering coil 716. The first centering coil 714, which has a larger inner diameter, fills additional annular space. As with the embodiment of FIG. 4, the multiple centering coil embodiment of FIG. 8 can beneficially fill the annular space even though the core 703 has a variable, tapering outer diameter.

The guidewire 700 of FIG. 8 also provides an example in which a centering coil 714 has a proximal end 705 that extends to a proximal end joint 707 at the proximal end of the tube 704 or even proximally beyond the proximal end joint 707. Forming the proximal end joint 707 near the proximal end of the tube 704 may provide structural benefits to the guidewire, particularly in relatively larger sized guidewires (such as those where the tube 704 has an outer diameter of about 0.024 inches or more). For example, some guidewires include a core 703 formed with a large outer diameter discontinuity at the joint 707. The discontinuity (i.e., abrupt change in outer diameter) in the core 703 may be formed to minimize bending stiffness at the joint 707. However, if the diameter of the tube 704 is greater than the section of the core 703 at the joint 707, a radial space will remain between the tube 704 and the core 703 at the joint 707. As shown, the centering coil 714 may extend to fill this space and provide structure for mechanically coupling the core 703 to the tube 704 at the joint 707. The structural configuration thus beneficially allows for a reduction in the diameter of the core 703 to thereby avoid excessive bending stiffness at the joint 707 while also avoiding or minimizing outer diameter discontinuities across the joint 707.

Figure 9:
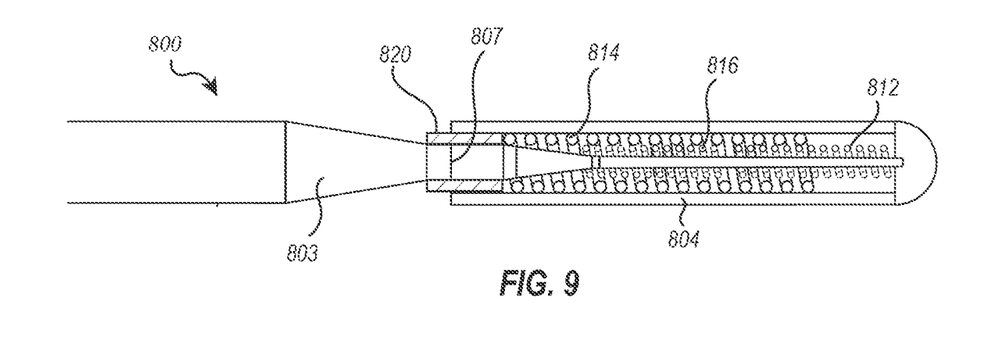
FIG. 9 illustrates another embodiment of a guidewire device including a bushing disposed between the core and the proximal end of the outer tube.

FIG. 9 illustrates another embodiment of a guidewire 800 having a bushing 820 disposed at or near the proximal end joint 807 to help fill space between the core 803 and tube 804 across the joint 807. The bushing 820 may therefore function similar to the proximal-most section of the centering coil 714 of FIG. 8. In this embodiment, the centering coil 814 does not extend to the proximal end of the tube 804. Rather, the centering coil 814 extends to the bushing 820, which then extends to the proximal end of the tube 804 or beyond the proximal end of the tube 804. The bushing 820 may be formed as a section of tube or braided material, for example, and may be formed of a suitable metal, alloy, or polymer. The guidewire 800 may otherwise be configured similar to other embodiments described herein, such as with a marker coil 812 and optionally a second centering coil 816, though the bushing 820 may also be utilized in other embodiments described herein.

Figure 10:
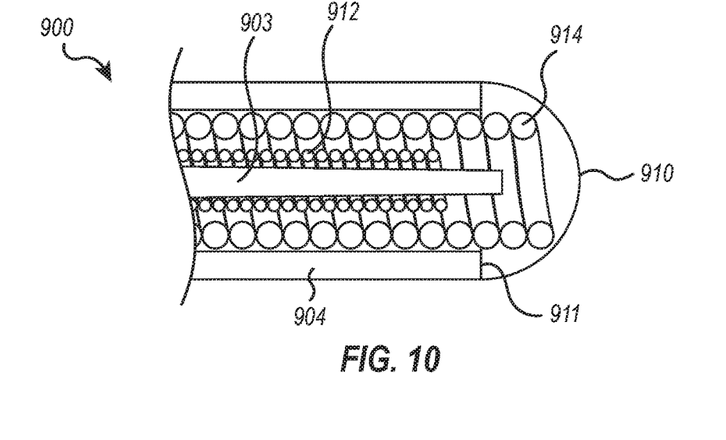
FIGS. 10 and 11 illustrate embodiments of a distal end of a guidewire device showing that the centering coil and/or marker coil components may be extended distally beyond the distal end of the outer tube.
Figure 11:
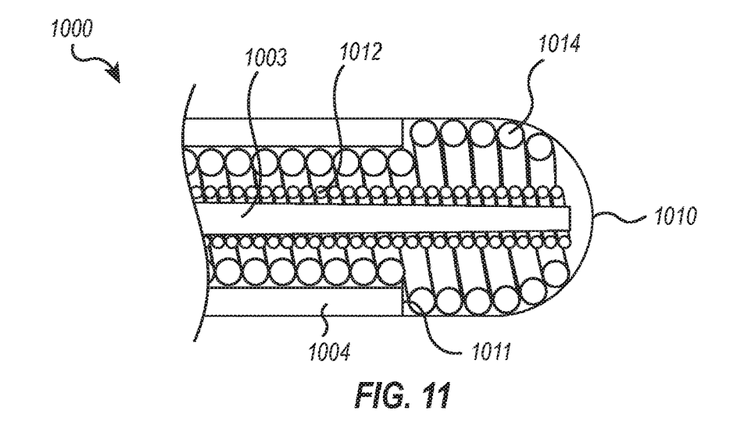

FIGS. 10 and 11 illustrate exemplary configurations of guidewire distal ends that may be utilized in the embodiments described herein. In FIG. 10, a guidewire 900 includes a centering coil 914 that extends beyond a distal end 911 of the tube 904 to form a portion of the distal tip 910. A marker coil 912 may also be disposed around the distal section of the core 903 and may also optionally extend beyond the distal end 911 of the tube 904. Extending the centering coil 914 beyond the distal end 911 of the tube 904 to form the distal tip 910 can provide a distal tip 910 with increased bending flexibility. The tube 904 can be chamfered, filleted, or otherwise reduced in diameter in the distal end portion to improve transitions in diameter. FIG. 11 illustrates another example of a guidewire 1000 with a centering coil 1014 that extends beyond a distal end 1011 of the tube 1004 to form a portion of the distal tip 1010. A marker coil 1012 may also be disposed around the distal section of the core 1003 and may also optionally extend beyond the distal end 1011 of the tube 1004. In this embodiment, the centering coil 1014 is wound so that the portion extending beyond the distal end 1011 of the tube 1004 has an outer diameter that substantially matches the outer diameter of the tube 1004. This beneficially prevents any discontinuities in the outer diameter of the device across the transition from the tube 1004 to the distal tip 1010.

Figure 12:
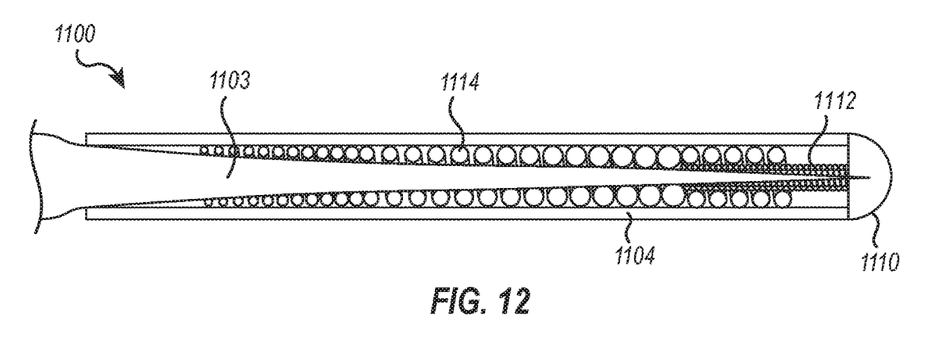
FIGS. 12 and 13 illustrate another embodiment of a guidewire device including a centering coil with an inner diameter that tapers to substantially conform to the core and/or marker coil.

FIG. 12 illustrates another embodiment of a guidewire 1100 having a centering coil 1114. In this embodiment, the centering coil 1114 is formed with a tapering inner diameter. The centering coil 1114 may, for example, be formed so that the inner diameter substantially matches the tapering profile of the core 1103. The centering coil 1114 can include an inner diameter that matches the tapering profile of the core 1103 while also having a substantially constant outer diameter. This type of structure beneficially fills the annular space between the core 1103 and the tube 1104 even though the core 1103 tapers. Any of the other centering coils described herein may be formed, in whole or in part, in this manner in order to better conform to diameter discontinuities in the core 1103. The guidewire 1100 may also include a marker coil 1112 disposed near the distal tip 1110. Where a marker coil 1112 is utilized, any portions of the centering coil 1114 coinciding with the marker coil 1112 may be formed so that the inner diameter of the centering coil 1114 allows sufficient space for the marker coil 1112.

Figure 13:
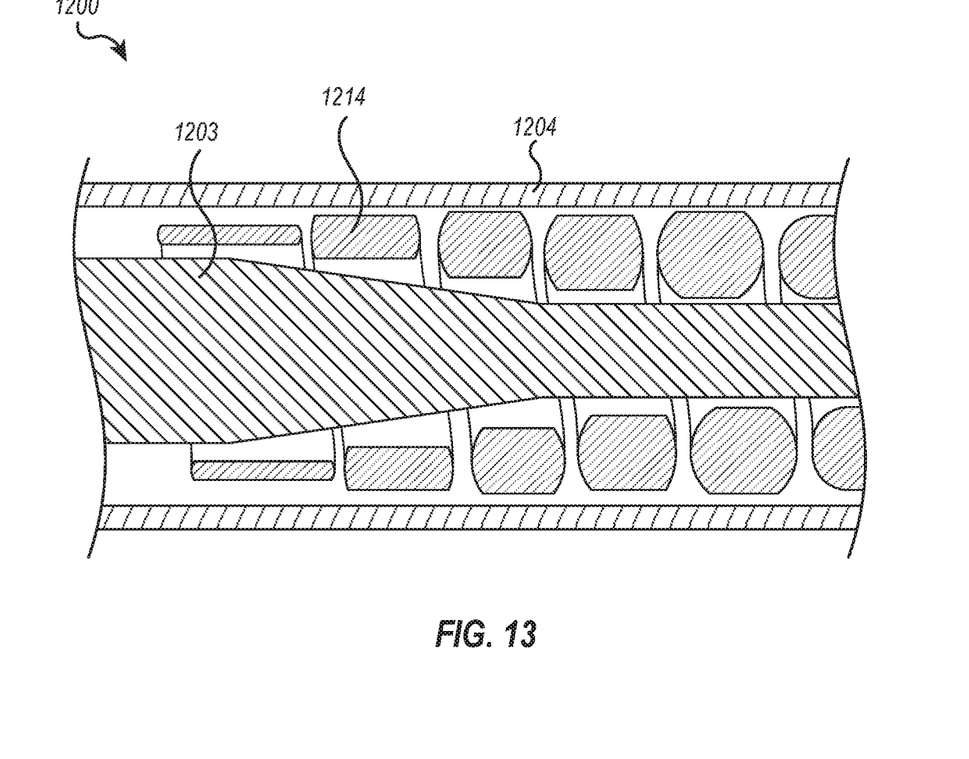

FIG. 13 illustrates another example of a section of a guidewire 1200 having a centering coil 1214 disposed within the annular space between the tube 1204 and the core 1203. As with the centering coil 1114 of FIG. 12, the centering coil 1214 is configured with a substantially constant outer diameter and a variable inner diameter for better conforming to the tapering shape of the core 1203. The centering coil 1214 may be formed, for example, by providing a constant diameter wire and selectively rolling the wire and wrapping on a tapered mandrel to obtain a variable inner diameter coil. As shown, the more proximal sections of the centering coil 1214, which are located where the annular space is relatively smaller, may be rolled/flattened to a greater degree than the more distal sections of the centering coil.

The centering mechanisms described herein may provide additional benefits independent of the centering functions described above. For example, it has been found that the application of a coating (e.g., a hydrophilic polymer or other suitable coating) to the outer surface of the tube is made more effective when a centering mechanism is utilized as opposed to when a centering mechanism is omitted. Without being bound to any particular theory, it is believed that the presence of a centering mechanism within the annular space modulates the flow of the coating during application and leads to a more even finish along the exterior surfaces of the tube. In the absence of a centering mechanism, the coating material may be more prone to pass through fenestrations in the tube toward the interior surface in an uneven manner. By better filling the annular space and minimizing differences in the size of unfilled annular space across the length of the tube, the coating appears to more evenly reside and polymerize or cure along the tube.

Figure 14A:
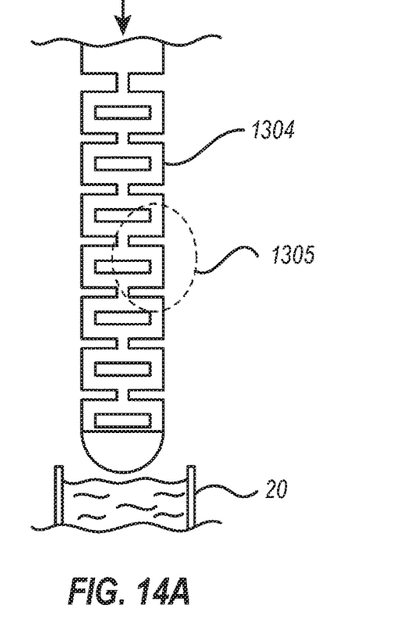
FIGS. 14A through 14C illustrate a coating process and the resulting coating layer on a micromachined tube, showing the difference in coating layer uniformity between a device not including a centering mechanism and a device including a centering mechanism.
Figure 14B:
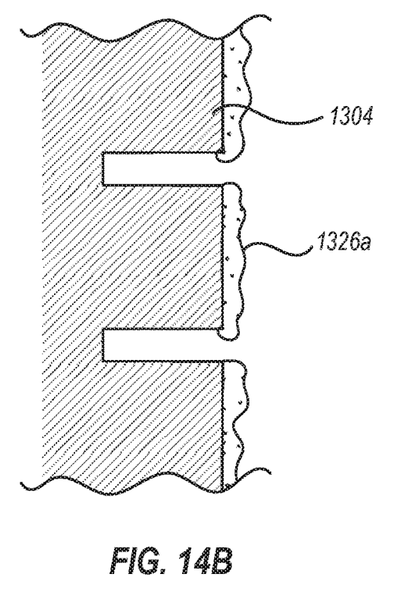
Figure 14C:
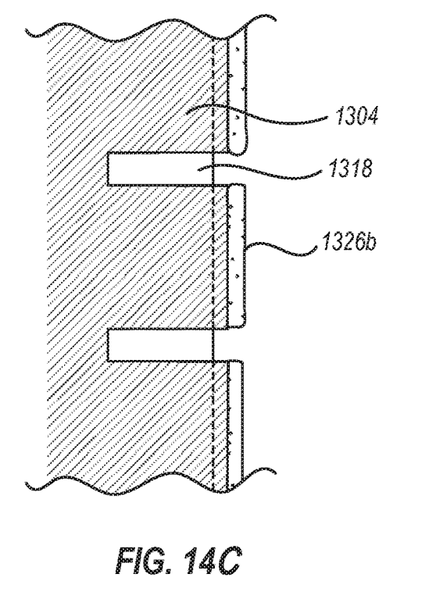

The enhanced coating uniformity provided by a centering mechanism is illustrated schematically by FIGS. 14A through 14C. FIG. 14A shows a typical dip coating process, though the coating uniformity benefits provided by a centering mechanism may also be realized in other coating processes such as spray coating. In a dip coating process, the tube 1304 is inserted and then drawn out of the polymer 20. FIGS. 14B and 14C are enlarged views of area 1305 of tube 1304. FIG. 14B illustrates a typical coating layer 1326a when applied to a device without a centering mechanism, whereas FIG. 14C illustrates a coating layer 1326b when applied to a device including a centering mechanism 1318. The centering mechanism 1318 may comprise any of the exemplary centering structures described herein or a combination thereof, such as one or more coils, tubes, polymer fillers, or a combination thereof.

As shown in FIG. 14B, the coating layer 1326a tends to form "globs" that reduce the uniformity of the layer when no centering mechanism is utilized. In contrast, as shown in FIG. 14C, the coating layer 1326b forms with greater relative uniformity when a centering mechanism 1318 is present. Greater uniformity of the coating layer is beneficial because the clearance between the outer diameter of a guidewire and the inner diameter of a catheter is typically rather small. The "bumps" in the coating layer 1326a effectively increase the outer diameter in certain parts of the guidewire which can make passage through the catheter more difficult.

Greater uniformity in the coating layer 1326b allows for finer control of certain design features of the device. For example, by reducing or eliminating the need to account for bumps in the coating layer in the overall outer diameter of the device, the average thickness of the coating may be increased without exceeding a limit to the overall outer diameter of the device. Additionally, or alternatively, the tube 1304 may be enlarged without exceeding a limit to the overall outer diameter of the device.

The centering mechanism principles described herein may be utilized with other structural configurations to provide beneficial centering effects. For example, while the above embodiments describe various centering mechanisms with a core wire "inner member" and a microfabricated tube "outer member," other structures may additionally or alternatively be utilized as the outer and/or inner members along with one or more of the described centering mechanisms. For example, the inner member may be a wire (such as a ground core as described above), a tube (e.g., metal or polymer hypotube or metal or polymer microfabricated tube), a braid, or a coil. By way of further example, the outer member may be a tube (e.g., metal or polymer hypotube or metal or polymer microfabricated tube), a braid, a coil, or a polymer tube impregnated with a braid or coil. The centering mechanism may be any one of those described herein or combination thereof, such as a coil, tube (e.g., metal or polymer hypotube or metal or polymer microfabricated tube), braid, or set of stacked rings.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An intravascular device, comprising:
a core having a proximal section and a distal section;
an outer tube coupled to the core such that the distal section of the core passes into and is encompassed by the outer tube, the outer tube and the core defining an annular space between an inner surface of the outer tube and an outer surface of the distal section of the core; and
first and second centering mechanisms positioned within at least a portion of the annular space, the first centering mechanism extending farther proximally than the second centering mechanism; and
radiopaque marker coil positioned within at least a portion of the annular space and positioned distal of the second centering mechanism,
wherein the first and second centering mechanisms are configured to limit movement of the core out of a radially centered position within the outer tube,
wherein the first and second centering mechanisms extend at least 15% of a length of the outer tube, and
wherein the first centering mechanism extends over the second centering mechanism and over at least a portion of the radiopaque marker coil.

2. The device of claim 1, wherein the first centering mechanism comprises a first centering coil.

3. The device of claim 2, wherein the first centering coil is not radiopaque.

4. The device of claim 2, wherein the first centering coil adjoins the core at a proximal coil joint, and wherein the proximal coil joint of the first centering coil is located at a point where the diameter of the core is approximately 20 to 80% of an inner diameter of the outer tube.

5. The device of claim 1, wherein the first centering mechanism comprises a first centering coil and the second centering mechanism comprises a second centering coil.

6. The device of claim 5, wherein the first centering coil and the second centering coil have different outside diameter to inside diameter ratios.

7. The device of claim 5, wherein the first centering coil has a pitch to coil wire diameter ratio of about 1.05 to 2.

8. The device of claim 5, wherein the second centering coil has a pitch to coil wire diameter ratio of about 1.05 to 2.

9. The device of claim 1, wherein the first centering mechanism, second centering mechanism, or both include an inner tube fully disposed within the outer tube.

10. The device of claim 9, wherein the inner tube of the first centering mechanism, second centering mechanism, or both are formed from the same material as the outer tube.

11. The device of claim 9, wherein the inner tube of the first centering mechanism, second centering mechanism, or both are formed as a polymer tube.

12. The device of claim 9, wherein the inner tube of the first centering mechanism, second centering mechanism, or both have a flexibility profile less than or equivalent to that of the outer tube.

13. The device of claim 1, wherein the first centering mechanism extends proximally beyond a proximal end of the tube, extends distally beyond a distal end of the tube, or both.

14. The device of claim 1, further comprising a coating layer applied at least to an outer surface of the tube, the coating layer having a more uniform thickness as compared to a coating layer of the device in the absence of a centering mechanism.

15. An intravascular device, comprising:
a core having a proximal section and a distal section;
an outer tube coupled to the core such that the distal section of the core passes into and is encompassed by the outer tube, the outer tube and the core defining an annular space between an inner surface of the outer tube and an outer surface of the distal section of the core;

a radiopaque marker coil positioned within at least a portion of the annular space; and first and second centering coils positioned within at least a portion of the annular space, the first centering coil extending farther proximally than the second centering coil, the first and second centering coils being configured to limit movement of the core out of a radially centered position within the outer tube, wherein the first and second centering coils are not radiopaque, wherein the radiopaque marker coil is positioned distal of the second centering coil, wherein the first centering coil extends over at least a portion of the radiopaque marker coil and extends over the second centering coil, and wherein a combined length of the first and second centering coils extends at least 15% of a length of the outer tube.

16. The device of claim 15, wherein the first centering coil and the second centering coil have different outside diameter to inside diameter ratios.

17. An intravascular device, comprising:

a core having a proximal section and a distal section;

an outer tube coupled to the core such that the distal section of the core passes into and is encompassed by the outer tube, the outer tube and the core defining an annular space between an inner surface of the outer tube and an outer surface of the distal section of the core; and first and second centering coils positioned within at least a portion of the annular space, the first centering coil extending farther proximally than the second centering coil, wherein the first and second centering coils are not radiopaque; and radiopaque marker coil positioned within at least a portion of the annular space and positioned distal of the second centering coil, wherein the first and second centering coils are configured to limit movement of the core out of a radially centered position within the outer tube, wherein the first and second centering coils extend at least 15% of a length of the outer tube, and wherein the first centering coil extends over the second centering coil and over at least a portion of the radiopaque marker coil.

18. The device of claim 17, wherein the first centering coil and the second centering coil have different outside diameter to inside diameter ratios.

* * * * *